(12) United States Patent
Reil

US011116991B2

(10) Patent No.: US 11,116,991 B2
(45) Date of Patent: *Sep. 14, 2021

(54) CORRECTION OF FEMALE URINARY INCONTINENCE AND SKIN REDUCTION

(71) Applicant: Julie Ann Reil, Billings, MT (US)

(72) Inventor: Julie Ann Reil, Billings, MT (US)

( * ) Notice: Subject to any disclaimer, the term of this patent is extended or adjusted under 35 U.S.C. 154(b) by 180 days.

This patent is subject to a terminal disclaimer.

(21) Appl. No.: 16/571,000

(22) Filed: Sep. 13, 2019

(65) Prior Publication Data
US 2020/0009399 A1 Jan. 9, 2020

Related U.S. Application Data

(63) Continuation of application No. 14/590,906, filed on Jan. 6, 2015, now Pat. No. 10,493,295, which is a (Continued)

(51) Int. Cl.
*A61B 5/06* (2006.01)
*A61N 5/06* (2006.01)
*A61K 31/192* (2006.01)
*A61K 33/00* (2006.01)
*A61K 33/12* (2006.01)
*A61K 33/24* (2019.01)
(Continued)

(52) U.S. Cl.
CPC .......... *A61N 5/0613* (2013.01); *A61K 31/192* (2013.01); *A61K 33/00* (2013.01); *A61K 33/12* (2013.01); *A61K 33/24* (2013.01); *A61K 33/26* (2013.01); *A61K 33/30* (2013.01); *A61K 36/02* (2013.01); *A61K 36/899* (2013.01); *A61N* 5/0616 (2013.01); *A61B 2017/00805* (2013.01); *A61K 31/60* (2013.01); *A61N 5/0603* (2013.01); *A61N 2005/0611* (2013.01); *A61N 2005/0659* (2013.01)

(58) Field of Classification Search
CPC .......................... A61N 5/06; A61N 2005/0659
See application file for complete search history.

(56) References Cited

U.S. PATENT DOCUMENTS 5,112,344 A 5/1992 Petros
5,620,478 A 4/1997 Eckhouse
(Continued)

FOREIGN PATENT DOCUMENTS

| CN | 1389241 | 1/2003 |
|---|---|---|
| DE | 296 11 520 | 9/1996 |
| EP | 1 038 505 | 9/2000 |

OTHER PUBLICATIONS

Reil, J., A New Application of an Infrared Light Based Device for Treatment of Stress Urinary Incontinence, Journal of Lasers in Surgery and Medicine, vol. 41, S21, A27 (Apr. 1, 2009).
(Continued)

*Primary Examiner* — Lynsey C Eiseman
(74) *Attorney, Agent, or Firm* — Davis Wright Tremaine LLP; George C. Rondeau, Jr.; Heather M. Colburn

(57) ABSTRACT

The invention relates to devices and compositions useful for and methods of female genital skin reduction, improvement of skin tone and treatment of female urinary incontinence, as well as the treatment or improvement of other clinical conditions, including but not limited to those involving the female genitalia.

22 Claims, 21 Drawing Sheets

Related U.S. Application Data continuation of application No. 13/079,729, filed on Apr. 4, 2011, now Pat. No. 8,961,577, which is a continuation-in-part of application No. 12/753,600, filed on Apr. 2, 2010, now abandoned, and a continuation-in-part of application No. 12/754,466, filed on Apr. 5, 2010, now abandoned.

(60) Provisional application No. 61/165,993, filed on Apr. 2, 2009.

(51) Int. Cl.

| | | |
|---|---|---|
| *A61K 33/26* | (2006.01) | |
| *A61K 33/30* | (2006.01) | |
| *A61K 36/02* | (2006.01) | |
| *A61K 36/899* | (2006.01) | |
| *A61B 17/00* | (2006.01) | |
| *A61K 31/60* | (2006.01) | |

(56) References Cited

U.S. PATENT DOCUMENTS

| | | | |
|---|---|---|---|
| 5,755,753 | A | 5/1998 | Knowlton |
| 5,899,909 | A | 5/1999 | Claren et al. |
| 5,957,920 | A | 9/1999 | Baker |
| 6,122,551 | A | 9/2000 | Rudie et al. |
| 6,165,440 | A | 12/2000 | Esenaliev |
| 6,251,753 | B1 | 6/2001 | Knowlton |
| 6,402,739 | B1 | 6/2002 | Neev |
| 6,406,423 | B1 | 6/2002 | Scetbon |
| 6,607,525 | B2 | 8/2003 | Franco |
| 6,740,107 | B2 | 5/2004 | Loeb |
| 7,112,171 | B2 | 9/2006 | Rocheleau et al. |
| 7,670,280 | B2 * | 3/2010 | Gloth ............ A61H 19/34 600/38 |
| 2001/0014819 | A1 | 8/2001 | Ingle et al. |
| 2004/0006334 | A1 | 1/2004 | Beyar et al. |
| 2006/0052847 | A1 | 3/2006 | Davenport et al. |
| 2006/0058712 | A1 | 3/2006 | Altshuler et al. |
| 2006/0282132 | A1 | 12/2006 | Arai et al. |
| 2007/0233191 | A1 | 10/2007 | Parmer |
| 2008/0125771 | A1 | 5/2008 | Lau et al. |
| 2009/0220423 | A1 | 9/2009 | Kurkayev |
| 2009/0319008 | A1 | 12/2009 | Mayer |
| 2010/0145321 | A1 | 6/2010 | Altshuler et al. |
| 2011/0060389 | A1 | 3/2011 | Reil |

OTHER PUBLICATIONS

Rogers, R.G., Urinar Stress Incontinence in Women, The New England Journal of Medicine, Mar. 6, 2008, 358:10, pp. 1029-1036.

Ruiz-Esparza, J., Near Painless, Nonablative, Immediate Skin Contraction Induced by Low-Fluence Irradiation with New Infrared Device: A Report of 25 Patients, Dermatological Surgery, 2006, 32(5) pp. 601-610.

Strohbehn, K., Shades of Dry—Curing Urinary Stress Incontincence, The New England Journal of Medicine, May 24, 2007, 356:21 pp. 2198-2200.

International Search Report and Written Opinion for International Application No. PCT/US2011/031125, dated May 27, 2011.

Office Action, dated Nov. 28, 2016, received in Canadian Patent Application No. 2,795,259.

Office Action, dated Sep. 25, 2017, received in Canadian Patent Application No. 2,795,259.

Extended European Search Report, dated Aug. 12, 2013, received in European Application No. 11 76 3565.

Office Action, dated Sep. 19, 2018, received in Canadian Application No. 2,795,259.

Information Disclosure Statement Transmittal filed herewith.

* cited by examiner

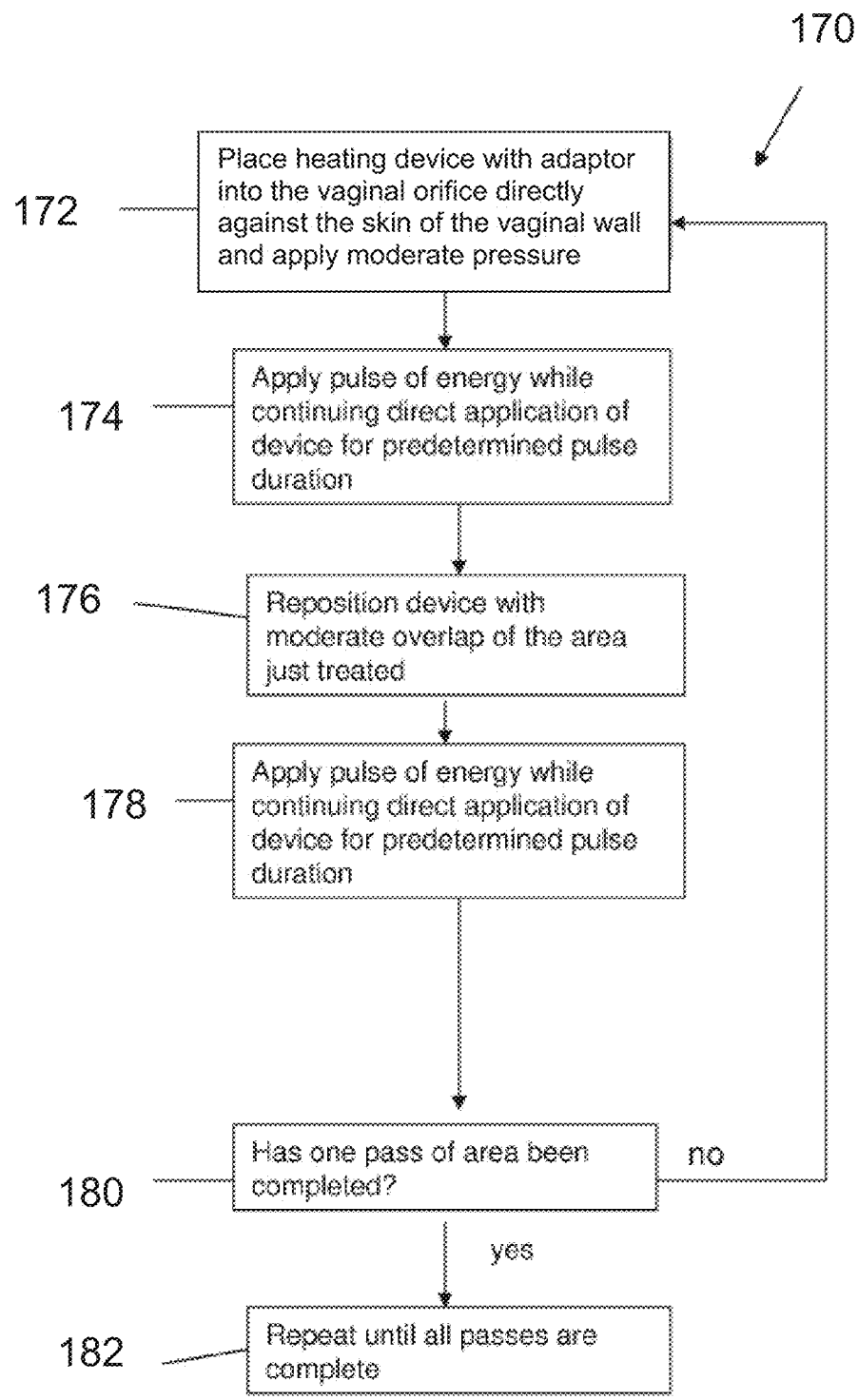

CORRECTION OF FEMALE URINARY INCONTINENCE AND SKIN REDUCTION

CROSS REFERENCE TO RELATED APPLICATION(S)

This application is a continuation of U.S. patent application Ser. No. 14/590,906 filed Jan. 6, 2015, which is a continuation of U.S. patent application Ser. No. 13/079,729 filed Apr. 4, 2011, which is a continuation-in-part of U.S. patent application Ser. No. 12/753,600, filed Apr. 2, 2010, which claims the benefit of U.S. provisional application No. 61/165,993, filed Apr. 2, 2009. U.S. patent application Ser. No. 14/590,906 is also a continuation-in-part of U.S. patent application Ser. No. 12/754,466, filed Apr. 5, 2010. The aforementioned applications are incorporated herein by reference in their entirety.

BACKGROUND OF THE INVENTION

Field of the Invention

The present invention is directed generally to methods of female genital skin reduction, improvement of skin tone and treatment of female urinary incontinence, as well as the treatment or improvement of other clinical conditions involving the female genitalia.

Description of the Related Art

The following description includes information that may be useful in understanding the present invention. It is not an admission that any of the information provided herein is prior art or relevant to the presently claimed invention, or that any publication specifically or implicitly referenced is prior art.

Urinary incontinence is a global problem afflicting an estimated 200 million people worldwide. Urinary incontinence is a stigmatized, underreported, under-diagnosed, under-treated medical condition that is erroneously thought to be a normal part of aging. Up to one in four women over the age of 18 experience episodes of leaking urine involuntarily. There are several forms of incontinence.

The type of incontinence that statistically affects most women, which is the focus of medical and surgical procedures for the correction of female incontinence—stress urinary incontinence—is the leaking of urine during physical movements such as coughing, sneezing, walking or exercising, when there is pressure on the bladder. Childbirth, menopause and aging can weaken the pelvic floor muscles, the vagina and the ligaments that support the bladder. When the supporting structures are weakened, the bladder and vaginal walls can move downward, altering the urethral position and keeping the muscles from squeezing as tightly as they normally could. Without a tightly sealed urethra, urine can leak during movements of physical stress.

Another type of incontinence—urge incontinence—involves losing urine after inappropriate bladder spasms or contractions of the detrusor muscle, usually at unexpected times such as touching or hearing the sound of water, during sleep, or after drinking water, is commonly treated with anti-cholinergic medications.

Yet another type of incontinence, and one which is very common among post-menopausal women, is mixed incontinence—a combination of stress and urge incontinence. Most women do not have pure stress or pure urge incontinence, and it has been suggested that mixed incontinence may be the most common type of urinary incontinence among women.

Much less common is a condition known as overactive bladder, which occurs when nerves send signals to the bladder at the wrong time, day and night, when the bladder is not full, causing the muscles to squeeze without warning.

Relatively rare in women are overflow incontinence, when the bladder doesn't empty properly causing urine to spill over, and functional incontinence, which happens to women with impaired thinking, moving or communicating making it hard for them to reach the toilet.

Transient incontinence is leaking that occurs temporarily due to a medication effect, urinary tract infection or restricted mobility from an injury. For example, a respiratory infection can trigger transient incontinence, which resolves when coughing ends.

Both stress and urge incontinence become more frequent with age and are most prevalent at the time of menopause, approximately age 50, and again at age 65. See R. G. Rogers, *Urinary Stress Incontinence in Women, N. Engl. J. Med.*, 358(10):1029-36 (Mar. 6, 2008). Obesity, multiple pregnancies/deliveries and white race are known to be risk factors for incontinence, with obese women having twice the risk of leaking compared to non-obese women. See K. Strohbehn, *Shades of dry—curing urinary stress incontinence, N. Engl. J. Med.*, 356(21):2198-200 (May 24, 2007; epub May 21, 2007).

The social costs of urinary incontinence are high and even mild symptoms will affect social, sexual, interpersonal, and professional function. Many women make adaptations to their activity level and even stop participating in exercise to avoid embarrassment, which impacts their health, overall fitness level and quality of life, Maintaining an active lifestyle is an important aspect to treating incontinence.

Incontinence can lead to feelings of shame and embarrassment and lead to low self esteem. Intimate relationships are often affected because of urine odor, pad use and frequent trips to the toilet. The fear of a major leaking accident when in public leads most incontinence sufferers to eventually become socially isolated. Fifty-three percent of homebound older persons are incontinent and more than half of all residents in nursing homes are incontinent, with incontinence being the second leading cause of institutionalization in the U.S. and the cost of caring for urinary incontinence in nursing facilities estimated at $5.3 billion.

The costs to our healthcare system and to society from incontinence are riveting. In 1995, the societal cost of incontinence for individuals over 65 years of age and older was $26.3 billion, or $3,565 per individual with urinary incontinence, with most of the total cost associated with direct treatment, such as diagnostic testing and medication.

The medical and surgical solutions for the problem of incontinence are invasive, require either local or general anesthesia, hospitalization, require time for recovery and healing, involve significant potential risks including hemorrhage, prolonged urinary retention, infection, urethral obstruction, de novo urge incontinence, damage to the surrounding tissue and erosion through tissue. The medical and surgical solutions presently available to women treat severe, daily symptoms of urinary incontinence but do not treat mild to moderate symptoms and do not treat preventatively.

Medical and surgical treatments for female urinary incontinence are customized methods aimed at improving either intrinsic urethral tone or improving extrinsic urethral tone, By way of example, U.S. Pat. No. 5,112,344 describes a method for surgical treatment of female urinary incontinence where a looping filamentary element is placed between the vaginal wall and rectus abdominis sheath and passed on each side of the urethra in an attempt to correct the urethral position by encouraging the development of a scar tissue, thereby improving extrinsic urethral support. Another example is U.S. Pat. No. 5,899,909, which discusses a surgical method used to treat female urinary incontinence where tape is passed into the body through the vagina on either side of the urethra to form a loop around the urethra, which is tightened and attached to the abdominal wall, in an attempt to give the urethra added extrinsic support and tone. Yet another example is U.S. Pat. No. 6,406,423, which describes another method for surgical treatment for urinary incontinence; this one, involving forming openings suprapubically and vaginally and forming tracks, verifying tracks by cystoscopy, passing a sleeved tape through these tracks to form a loop under the urethra, tightening the loop, removing the sleeve and leaving the tape implanted under the urethra, to give the urethra added extrinsic support and tone. Still another example is U.S. Pat. No. 7,112,171, which discusses a sling assembly with secure and convenient attachment, as an improved and potentially safer instrument for performing the urethral sling surgical method, a procedure involving placement of a sling made of mesh or tape to stabilize or support the urethra extrinsically. The sling procedure has potential complications of urethral obstruction, development of de novo urge incontinence, hemorrhage, prolonged urinary retention, infection and damage to the surrounding tissue and sling erosion.

There are other concerns regarding the sling device. Many midurethral slings and related devices have received approval from the FDA through a 510(k) process that does not require proof of safety and efficacy of the new device, but requires evidence that something similar has already been approved for use. After a particular sling device was approved through a 510(k) process and put into use before clinical trials were conducted, this device unfortunately resulted in erosion through the vaginal wall, causing pain and bleeding for women, and had to be removed from the market. See Strohbehn.

U.S. Pat. No. 5,957,920 discusses in its background other options for treatment of urinary incontinence, including injection of collagen around the urethra attempting to improve intrinsic tone of the urethra. This patent describes a method for treating urinary incontinence using radiofrequency waves to thermally damage cells of the internal urethra, thereby promoting scar tissue, attempting to improve intrinsic urethral tone.

Each of the aforementioned approaches to female genital skin reduction, improvement of skin tone and/or treatment of female urinary incontinence suffers from drawbacks. In fact, current methods for treatment of female urinary incontinence are invasive, require recovery time and are expensive. These methods also involve potential risks including the injection or placement of foreign substances or objects into the body, general anesthesia, overcorrection of the urethral tone leading to urethral obstruction, development of new urge incontinence, infection, hemorrhage, as well as scarring and erosion of a foreign body through the urethral tissues resulting in chronic pain and bleeding. Moreover, current methods of treatment of female urinary incontinence are not effective in preventing urinary incontinence, which is known to be a condition that progressively worsens as women advance in age through menopause and beyond.

There is a need for a completely non-invasive treatment for urinary incontinence and for a treatment that can be used to treat women in the early stages of incontinence as well as treat incontinence preventatively. The present invention overcomes the deficiencies and risks of previous medical and surgical procedures for female urinary incontinence, and also provides features and advantages not previously found in other methods and technologies. The present invention provides these and other advantages as will be apparent from the following detailed description and accompanying figures.

SUMMARY OF INVENTION

In an embodiment, the invention includes a method of treating, preventing, reducing the likelihood of developing, reducing the severity of and/or improving a condition in a subject in need thereof, comprising the steps of: providing a device comprising a light source, wherein the light source is configured to emanate infrared light or wherein the light source is a broadband spectrum light source; and applying a sequence of one or more pulses of light from the light source to an anatomical region in the subject to treat, prevent, reduce the likelihood of developing, reduce the severity of and/or improve the condition. The anatomical region may comprise tissue, skin, or another anatomical structure. The light source may have a spectrum of from 700 nm to 1,800 nm. The method may further comprise applying a layer of gel to the surface of the anatomical region before the step of applying the sequence of one or more pulses of light from the light source. The method may further comprise removing most of the gel from the surface of the anatomical region after the step of applying the sequence of one or more pulses of light from the light source. The method may further comprise, after the step of removing most of the layer of gel, the step of applying one or more additional sequences of one or more pulses of light from the light source to the anatomical region in the subject. The method may further comprise, before applying each of the one or more additional sequences of one or more pulses of light from the light source, applying a new layer of gel to the surface of the anatomical region; and after applying each of the one or more additional sequences of one or more pulses of light from the light source, removing most of the gel from the surface of the anatomical region. The gel may be a cooled ultrasound gel. The method may further comprise applying a composition to the surface of the anatomical region before the steps of applying the layer of gel and applying the new layer of gel, and wherein the steps of removing most of the gel further comprise removing most of the composition. The composition may comprise micronized zinc oxide, micronized titanium dioxide, pigmenting titanium dioxide, iron oxide, oat, rice, mica, silicone powder, marine algae and/or talc. The composition may be in the form of a powder. The composition may be formulated to comprise particles of varying size to reflect, refract and/or scatter light in a predetermined manner. The composition may further comprise salicylic acid. The condition may be selected from the female genital skin reduction, skin tone, and combinations thereof. The condition may be selected from urinary holding capacity, urinary control, urethral tone, urethral position, involuntary leaking of urine, and combinations thereof. The condition may be selected from perineal scars, external hemorrhoids, rectal holding capacity, anterior vaginal wall tone, cystocele, posterior vaginal wall tone, rectocele, vulvar varicosities, pelvic muscle tone, skin condition or health, vaginal prolapse, rectal prolapse, and combinations thereof. The condition may be selected from female urinary incontinence, stress urinary incontinence, urge urinary incontinence, mixed urinary incontinence, overflow incontinence, and combinations thereof. The anatomical region may be labia majora, labia minora, prepuce of clitoris, periurethral skin, urethral skin, vagina introitus, perineum, anus, perianus, vaginal wall, and combinations thereof.

In another embodiment, the invention includes an apparatus, comprising a first end adapted to mechanically interact with a device that emits infrared light; a second end; an opaque shaft positioned between the first end and the second end; an opening configured on the shaft, adapted to allow the transmission of infrared light therethrough; and means for transmitting infrared light from the first end through the shaft to the opening. The means for transmitting infrared light may be selected from one or more crystals, mirrors, prisms, lenses, and combinations thereof. The apparatus may be adapted to be rotatably and/or removably attached to the device that emits infrared light. The apparatus may be configured to be inserted into an orifice in a human body and to apply infrared light to a surface thereof. In another embodiment, the invention includes, in combination, the apparatus and the device that emits infrared light.

In another embodiment, the invention includes an apparatus, comprising an elongated light source to transmit infrared light; and a mechanism in mechanical communication with the elongated light source adapted to mechanically interact with a device that emits infrared light, wherein the elongated light source is configured to be inserted into an orifice in a human body and to apply infrared light transmitted through the elongated light source to a surface of the human body. The elongated light source may be selected from crystals and sapphire crystals. The apparatus may further comprise an opaque cap positioned on the elongated light source on the end distal from the mechanism to prevent light transmitted through the elongated light source from travelling in an axial direction therefrom. In another embodiment, the invention includes, in combination, the apparatus and the device that emits infrared light.

BRIEF DESCRIPTION OF THE SEVERAL VIEWS OF THE DRAWING(S)

Exemplary embodiments are illustrated in referenced figures. It is intended that the embodiments and figures disclosed herein are to be considered illustrative rather than restrictive.

Figure 4A:
Figure 4B:

FIG. 4A is a photograph of female genitalia prior to treatment, and FIG. 4B is a photograph of the same female genitalia after treatment, illustrating reduction and toning in skin of labia majora, labia minora, clitoral hood, vaginal introitus, perineum and anus in accordance with an embodiment of the present invention. FIGS. 4A and 4B also illustrate improvement of skin condition, vulvar varicosities, anterior vaginal wall tone and cystocele as well as treatment of vaginal prolapse in accordance with an embodiment of the present invention.

Figure 5A:
Figure 5B:

FIG. 5A is a photograph of female genitalia prior to treatment, and FIG. 5B is a photograph of the same female genitalia after treatment, illustrating reduction and toning in skin of labia majora, labia minora, clitoral hood and perineum in accordance with an embodiment of the present invention.

Figure 6A:
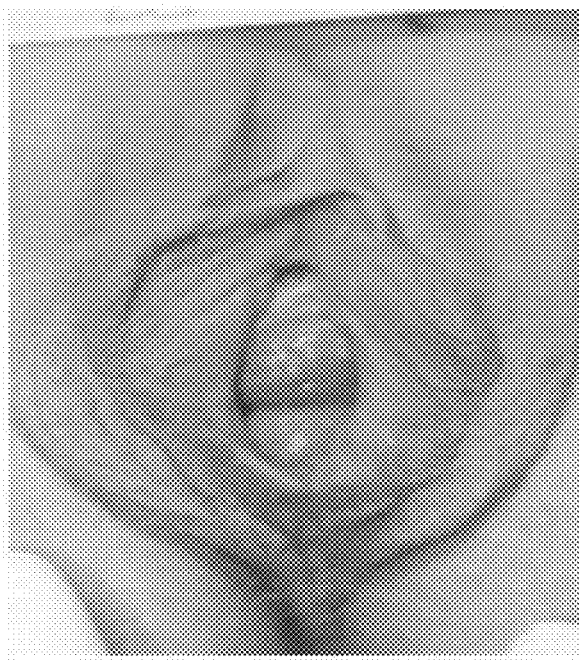
Figure 6B:
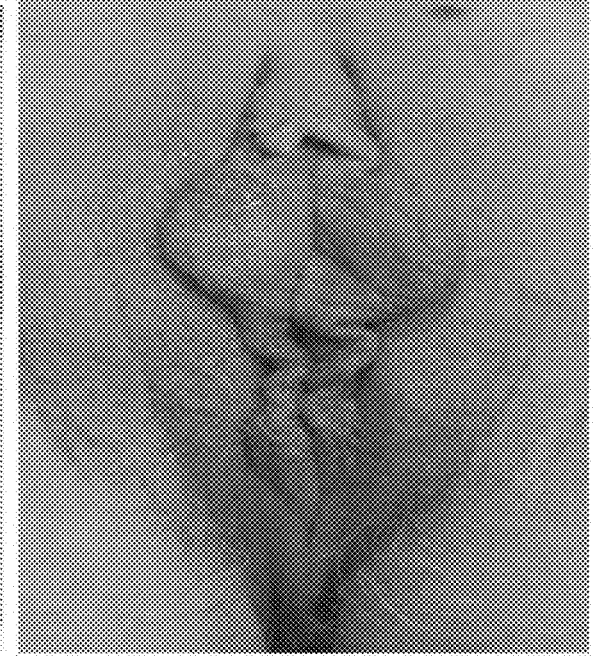

FIG. 6A is a photograph of female genitalia prior to treatment, and FIG. 6B is a photograph of the same female genitalia after treatment, illustrating reduction and toning in skin of labia majora, labia minora, clitoral hood, vaginal introitus in accordance with an embodiment of the present invention. FIGS. 6A and 6B also illustrate improvement in anterior vaginal wall tone and cystocele, improvement in posterior vaginal wall tone and rectocele and treatment of vaginal prolapse in accordance with an embodiment of the present invention.

Figure 7:
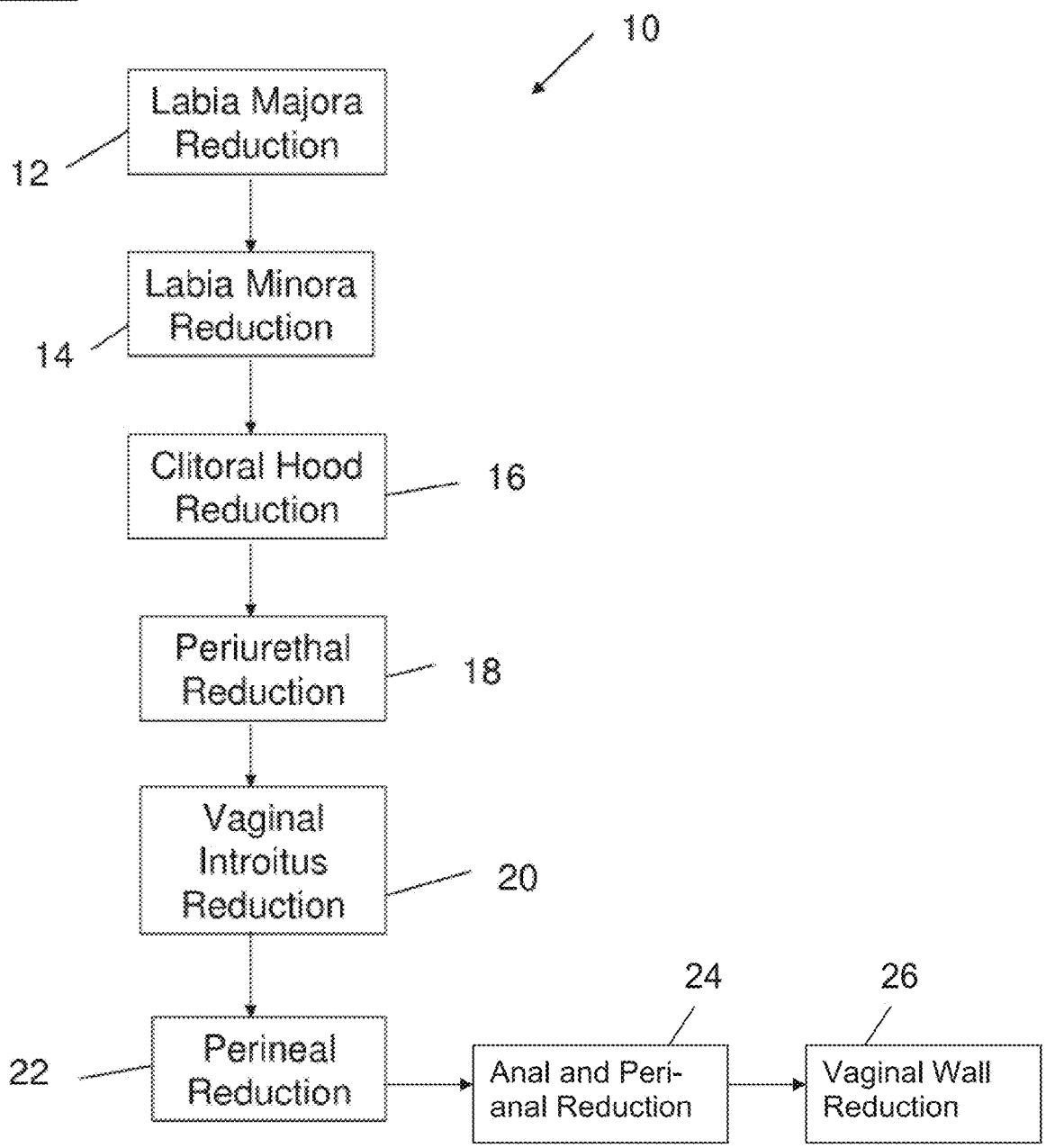

FIG. 7 is a flow chart 10 for implementing an exemplary method, in accordance with an embodiment of the present invention.

Figure 8:
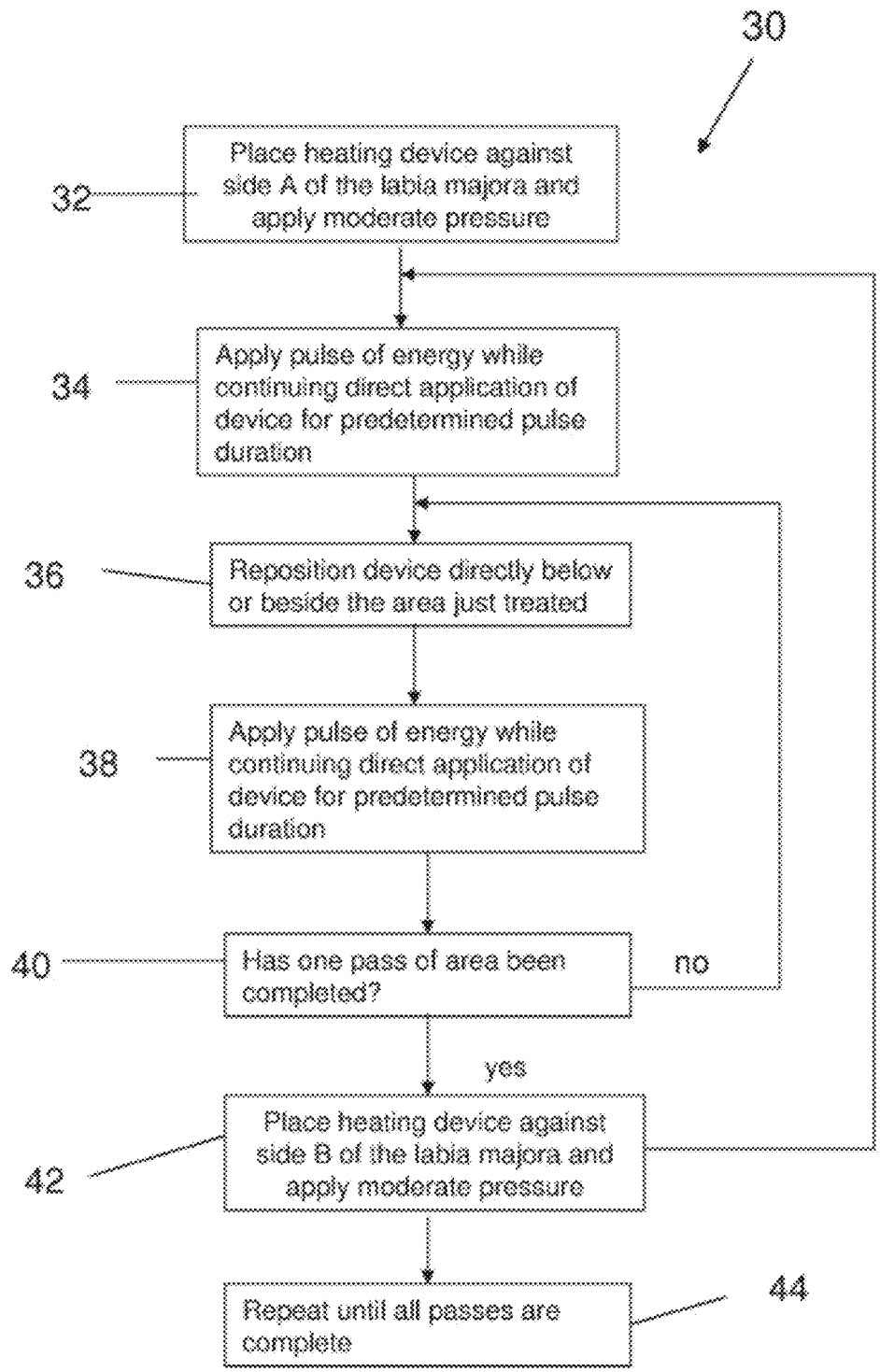

FIG. 8 is a flow chart 30 for implementing the exemplary method for labia majora reduction, in accordance with an embodiment of the present invention.

Figure 9:
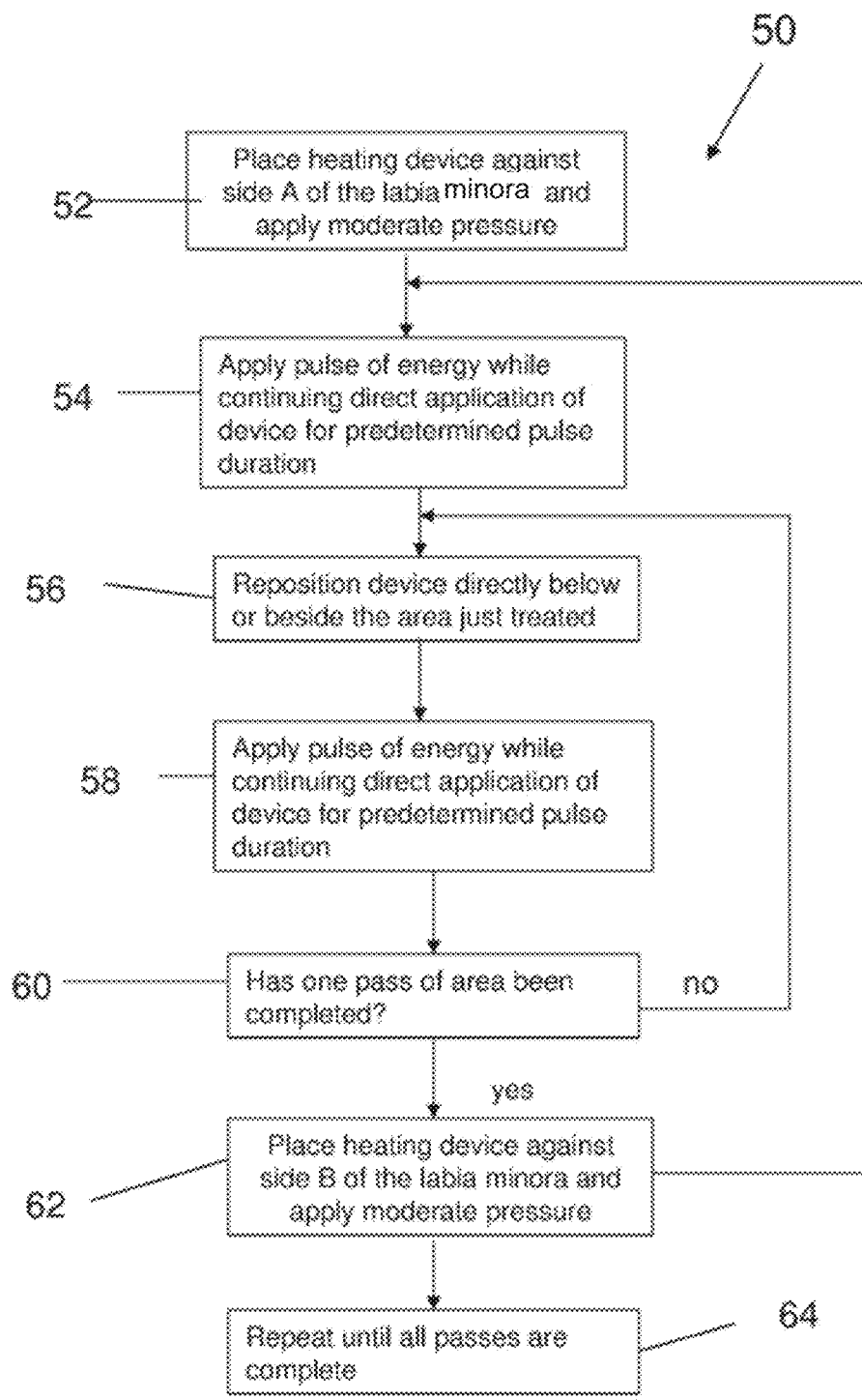

FIG. 9 is a flow chart 50 for implementing the exemplary method for labia minora reduction, in accordance with an embodiment of the present invention.

Figure 10:
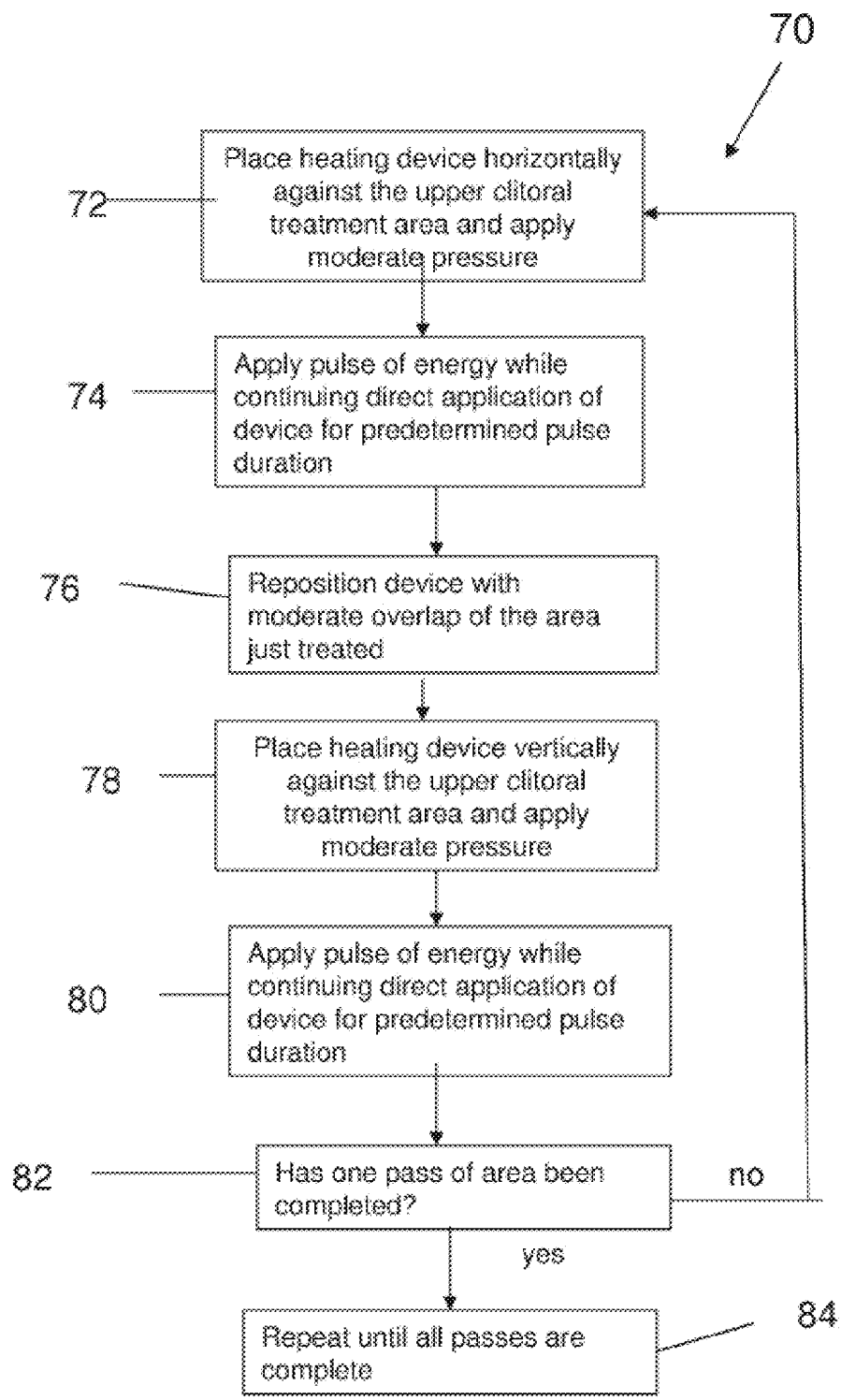

FIG. 10 is a flow chart 70 for implementing the exemplary method for clitoral hood reduction, in accordance with an embodiment of the present invention.

Figure 11:
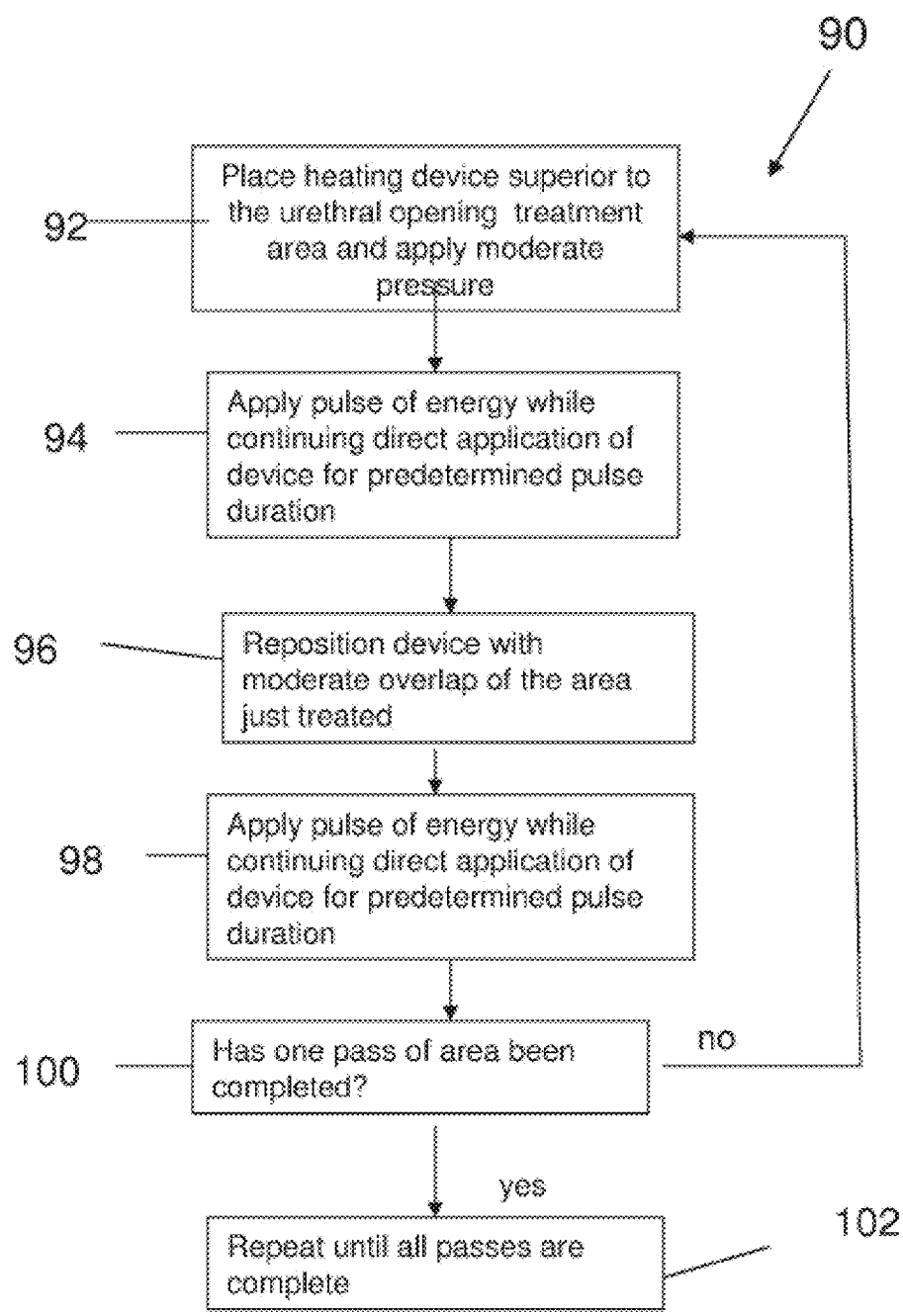

FIG. 11 is a flow chart 90 for implementing the exemplary method for periurethral reduction, in accordance with an embodiment of the present invention.

Figure 12:
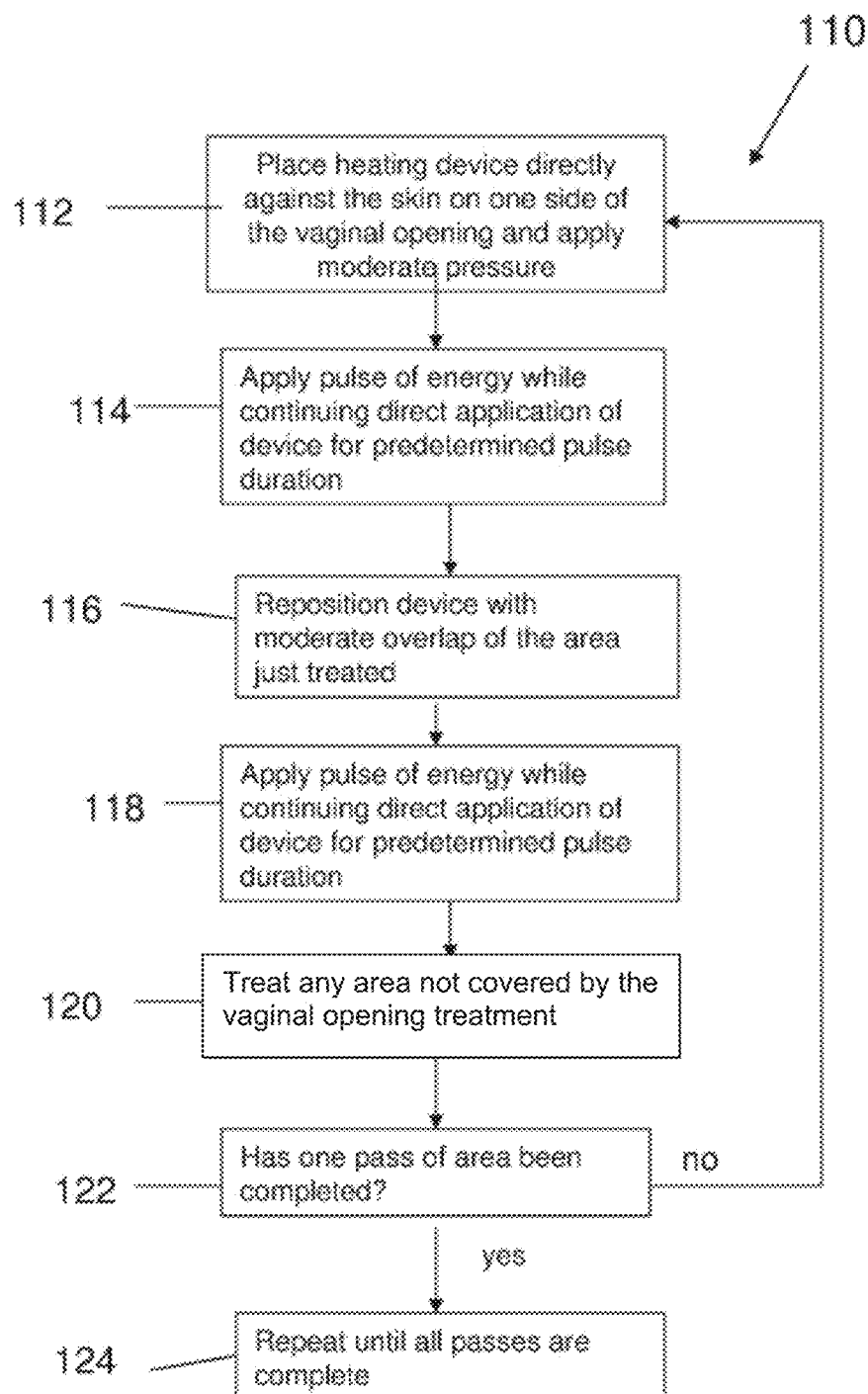

FIG. 12 is a flow chart 110 for implementing the exemplary method for vaginal introitus reduction, in accordance with an embodiment of the present invention.

Figure 13:
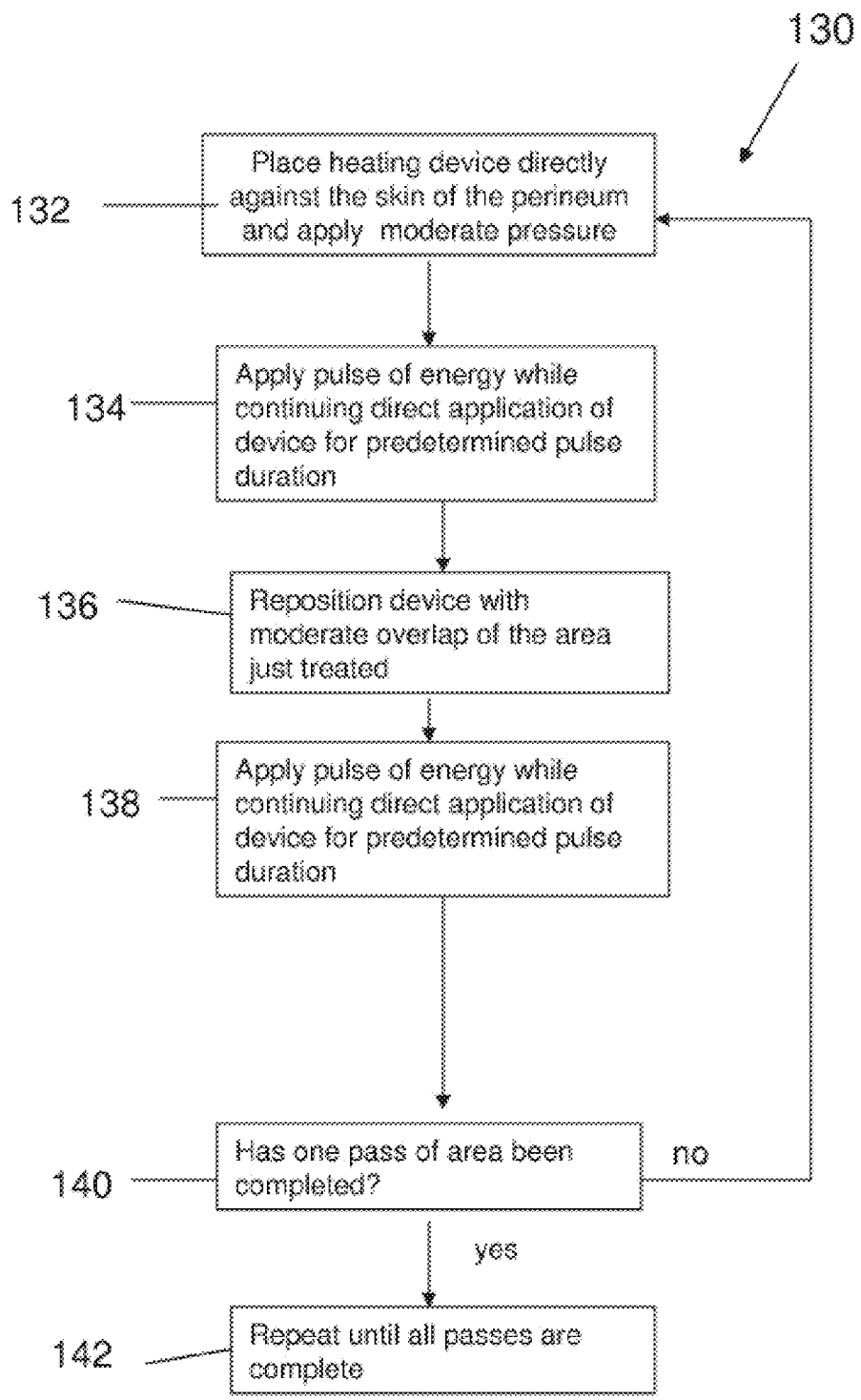

FIG. 13 is a flow chart 130 for implementing the exemplary method for perineal reduction, in accordance with an embodiment of the present invention.

Figure 14:
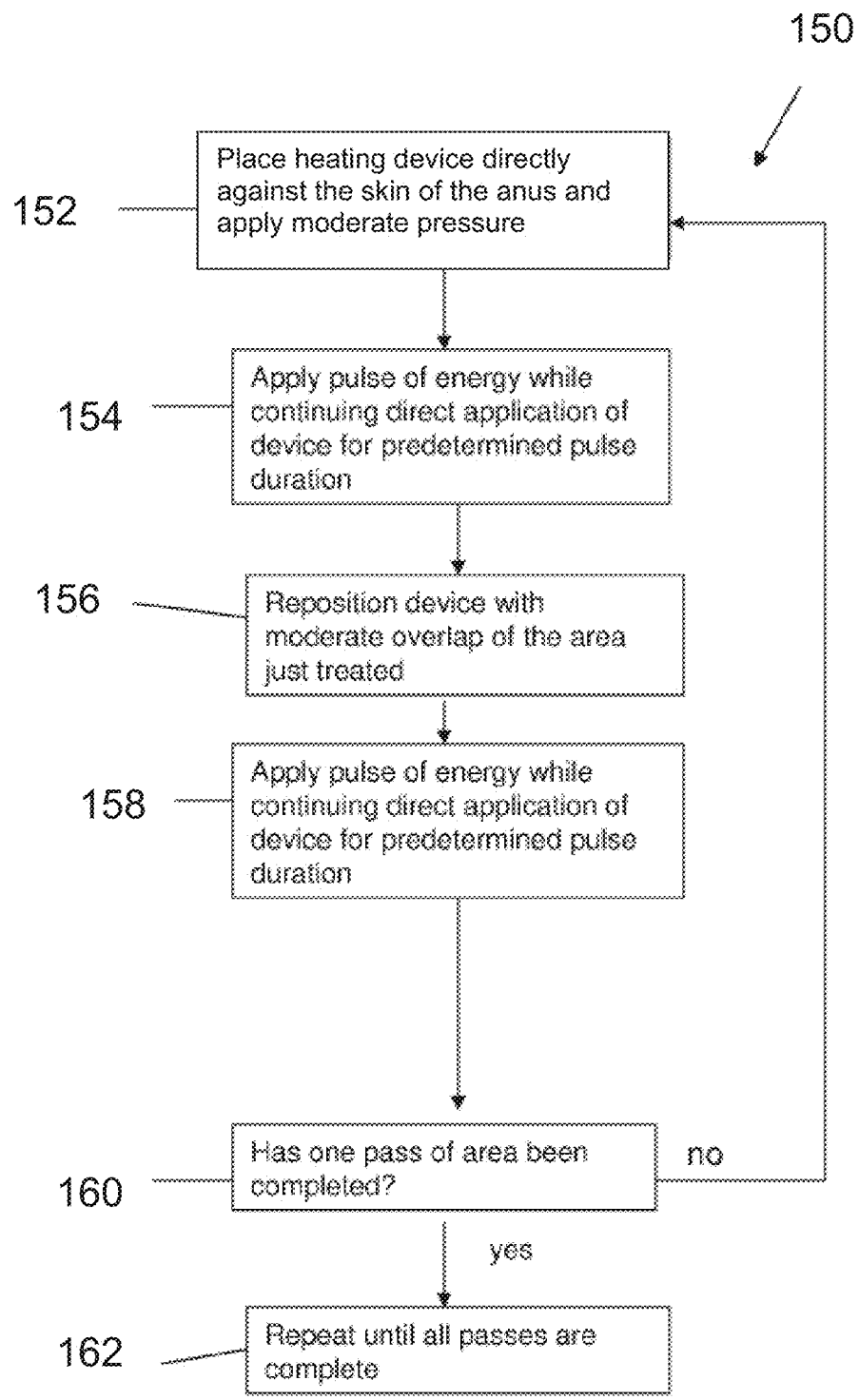

FIG. 14 is a flow chart 150 for implementing the exemplary method for anal reduction, in accordance with an embodiment of the present invention.

FIG. 15 is a flow chart 170 for implementing the exemplary method for vaginal wall reduction, in accordance with an embodiment of the present invention.

Figure 16A:
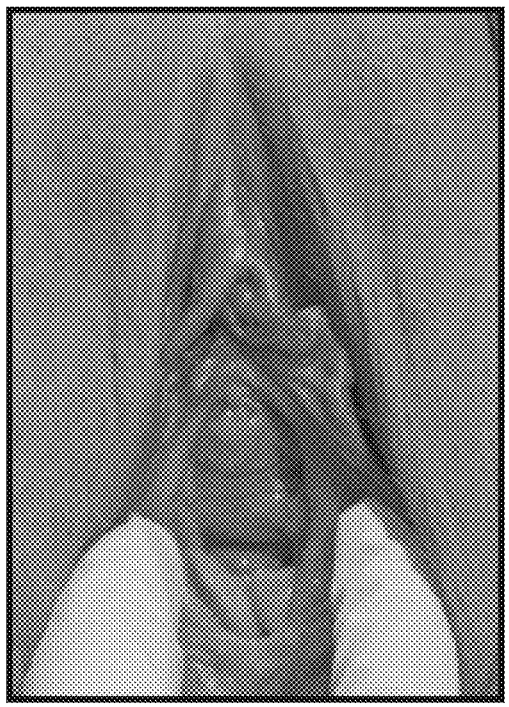
Figure 16B:
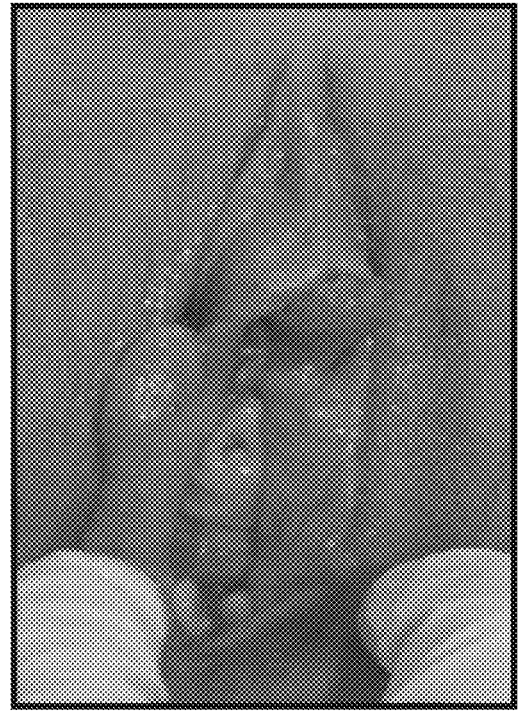

FIG. 16A is a photograph of female genitalia prior to treatment, and FIG. 16B is a photograph of the same female genitalia after treatment, illustrating reduction and toning in skin of labia minora, clitoral hood, urethral opening and vaginal introitus in accordance with an embodiment of the present invention. FIGS. 16A and 16B also illustrate improvement in urethral tone, urethral position and anterior vaginal wall tone and cystocele in accordance with an embodiment of the present invention.

Figure 17A:
Figure 17B:
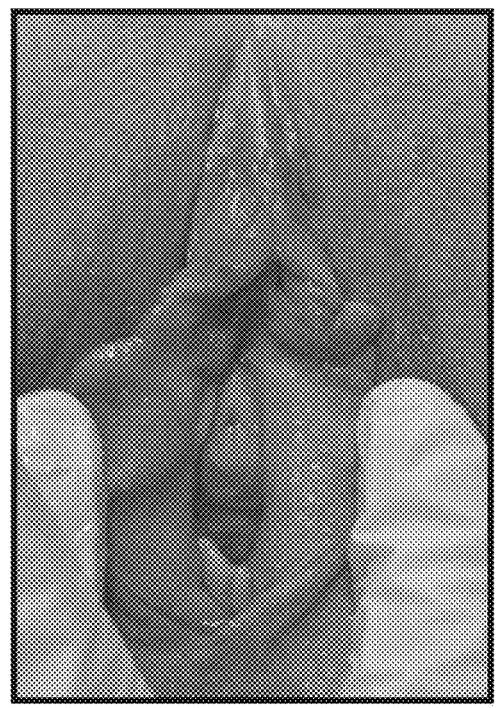

FIG. 17A is a photograph of female genitalia prior to treatment, and FIG. 17B is a photograph of the same female genitalia after treatment, illustrating reduction and toning in skin of labia minora, clitoral hood, urethral opening and vaginal introitus in accordance with an embodiment of the present invention. FIGS. 17A and 17B also illustrate improvement in urethral tone, urethral position and anterior vaginal wall tone and cystocele in accordance with an embodiment of the present invention.

Figure 18A:
Figure 18B:

FIG. 18A is a photograph of female genitalia prior to treatment, and FIG. 18B is a photograph of the same female genitalia after treatment, illustrating reduction and toning in skin of urethral opening and vaginal introitus in accordance with an embodiment of the present invention. FIGS. 18A and 18B also illustrate improvement in urethral tone and urethral position in accordance with an embodiment of the present invention.

Figure 19A:
Figure 19B:
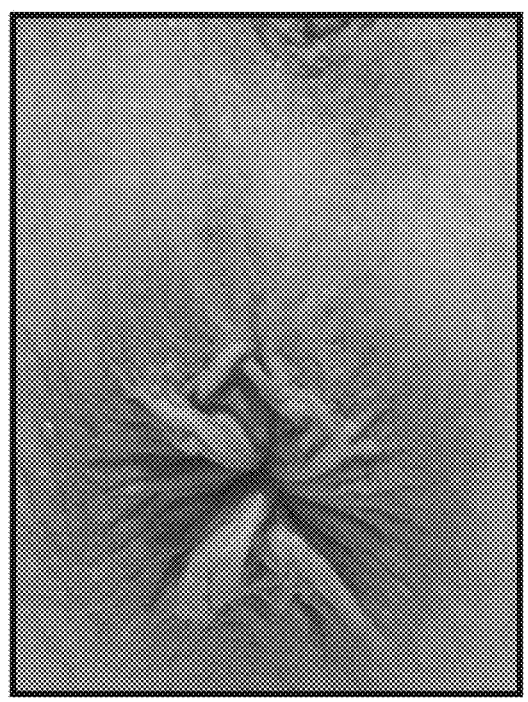

FIG. 19A is a photograph of female genitalia prior to treatment, and FIG. 19B is a photograph of the same female genitalia after treatment, illustrating reduction and toning in skin of perineum and anus in accordance with an embodiment of the present invention. FIGS. 19A and 19B also illustrate improvement perineal scarring in accordance with an embodiment of the present invention.

Figure 20A:
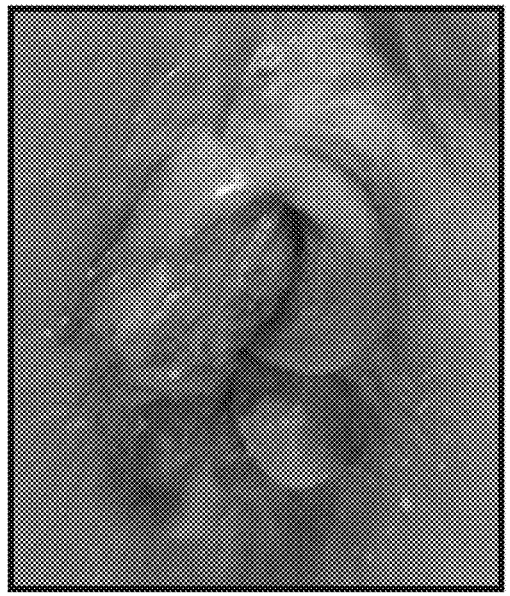
Figure 20B:

FIG. 20A is a photograph of female genitalia prior to treatment, and FIG. 20B is a photograph of the same female genitalia after treatment, illustrating improvement in an external hemorrhoid in accordance with an embodiment of the present invention.

Figure 21A:
Figure 21B:
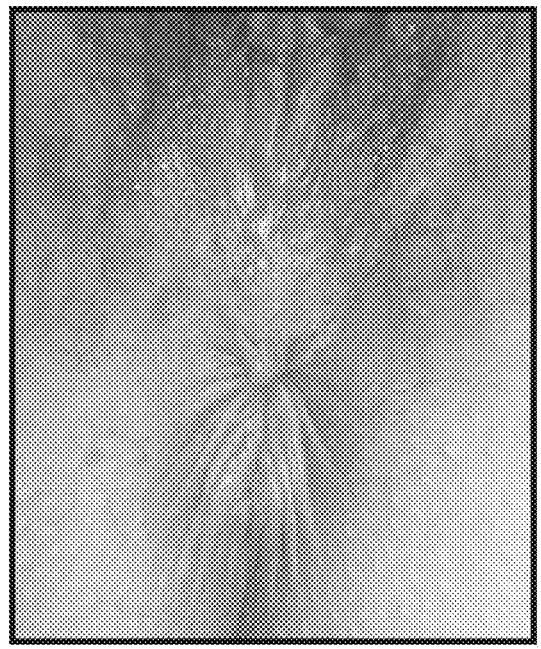

FIG. 21A is a photograph of female genitalia prior to treatment, and FIG. 21B is a photograph of the same female genitalia after treatment, illustrating reduction and toning of skin of anus in accordance with an embodiment of the present invention.

Figure 22A:
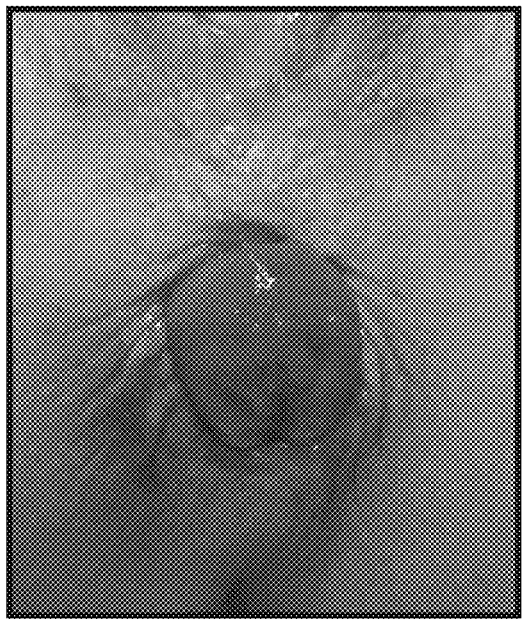
Figure 22B:

FIG. 22A is a photograph of female genitalia prior to treatment, and FIG. 22B is a photograph of the same female genitalia after treatment, illustrating reduction and toning of skin of anus in accordance with an embodiment of the present invention. FIGS. 22A and 22B also illustrates treatment of rectal prolapse in accordance with an embodiment of the present invention.

Figure 23A:
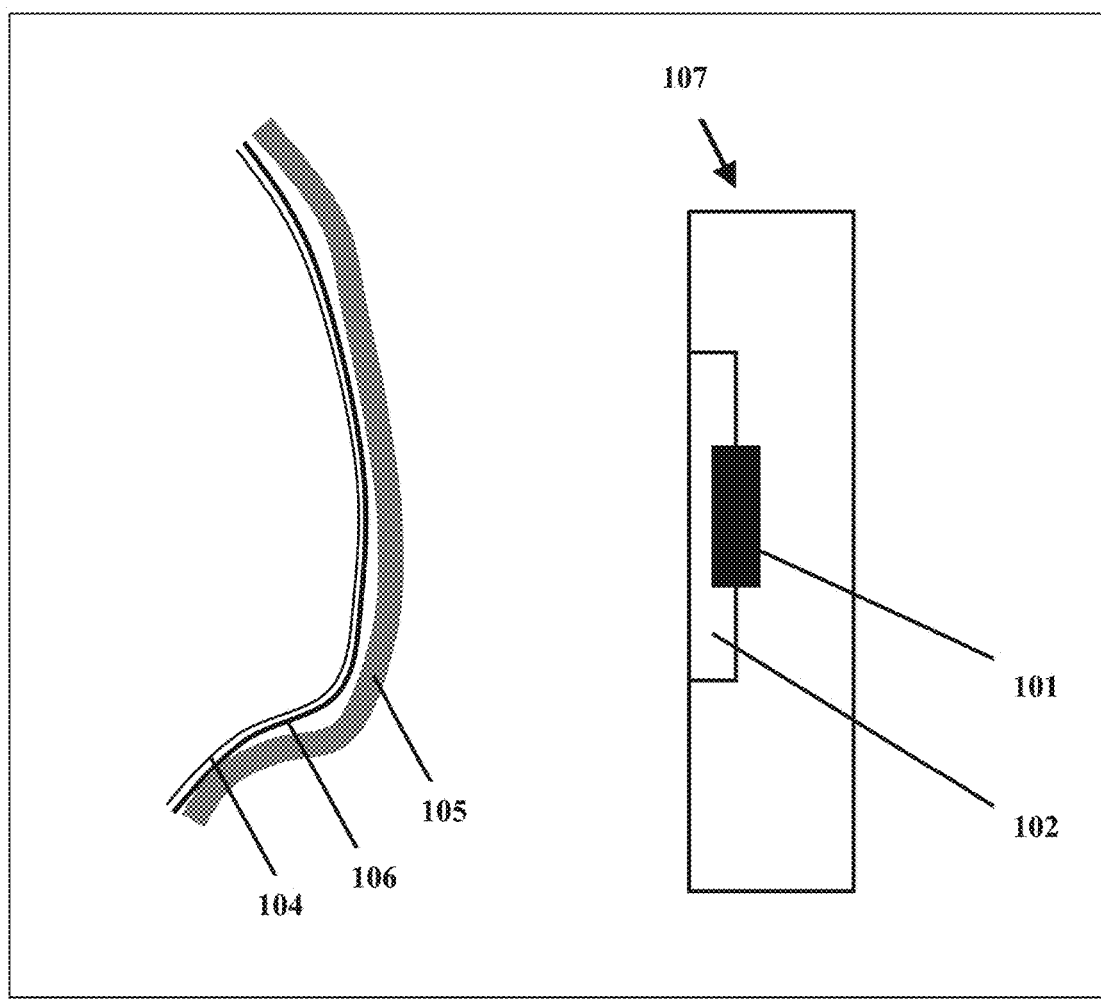
Figure 23B:
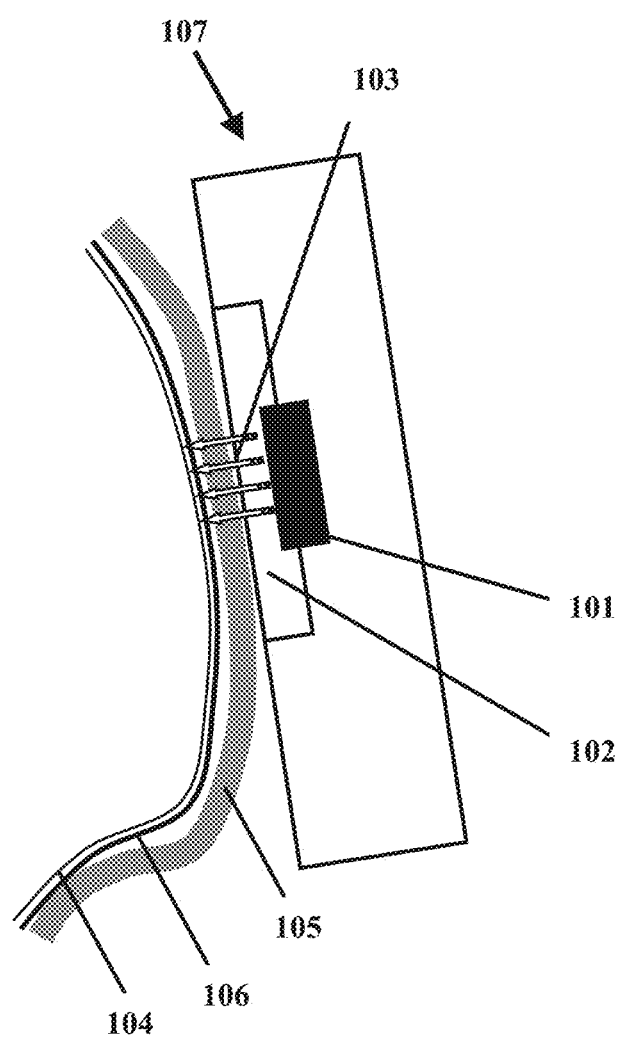

FIGS. 23A and 23B depict a device emitting light in connection with a treatment protocol, in accordance with an embodiment of the invention.

Figure 24A:
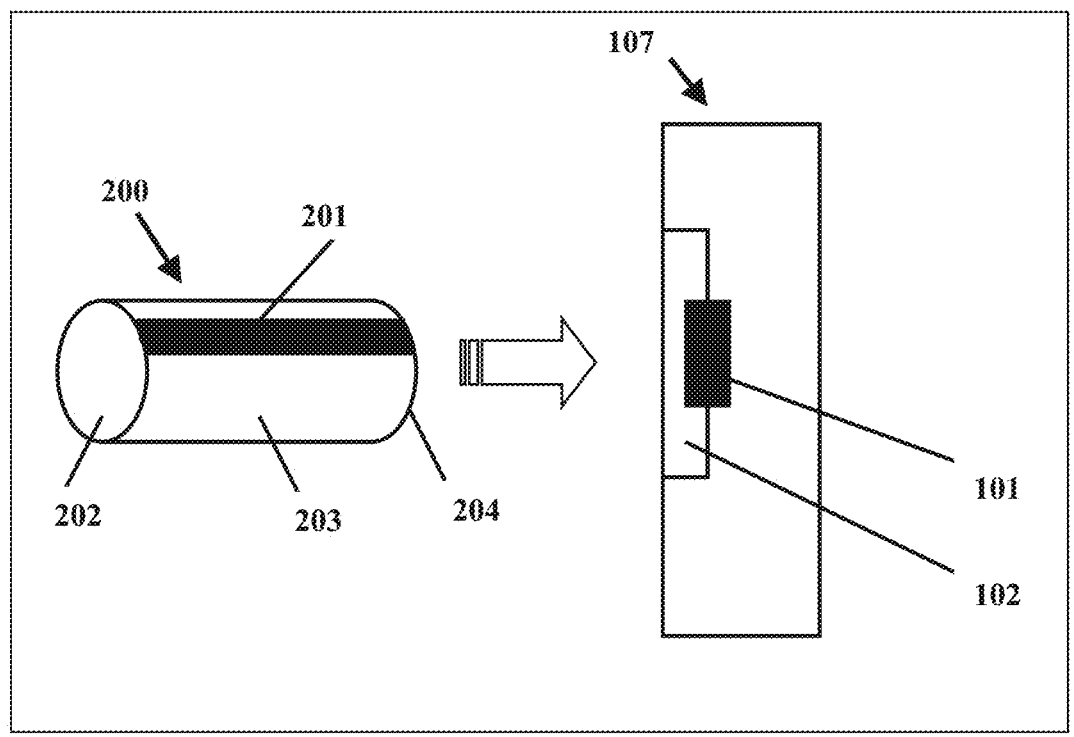
Figure 24B:
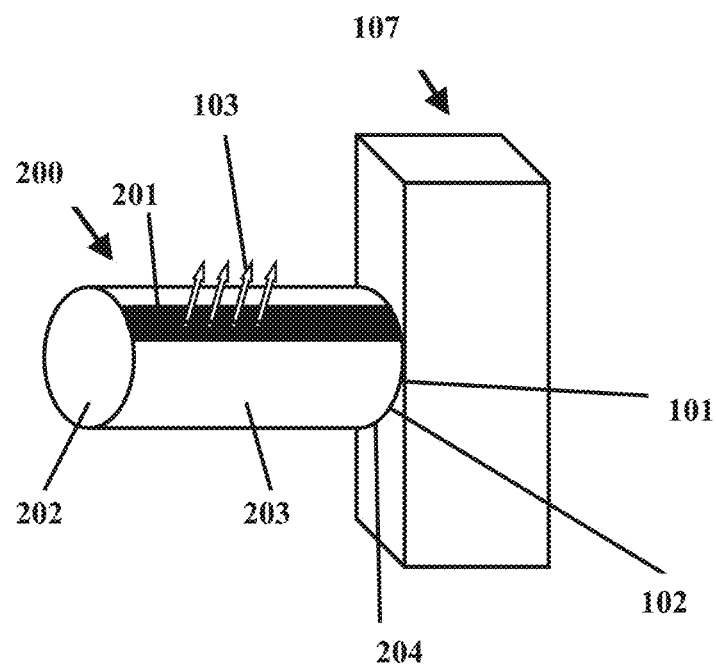

FIGS. 24A and 24B depict an adaptor to operate with a device emitting light in connection with a treatment protocol, in accordance with an embodiment of the invention.

Figure 25A:
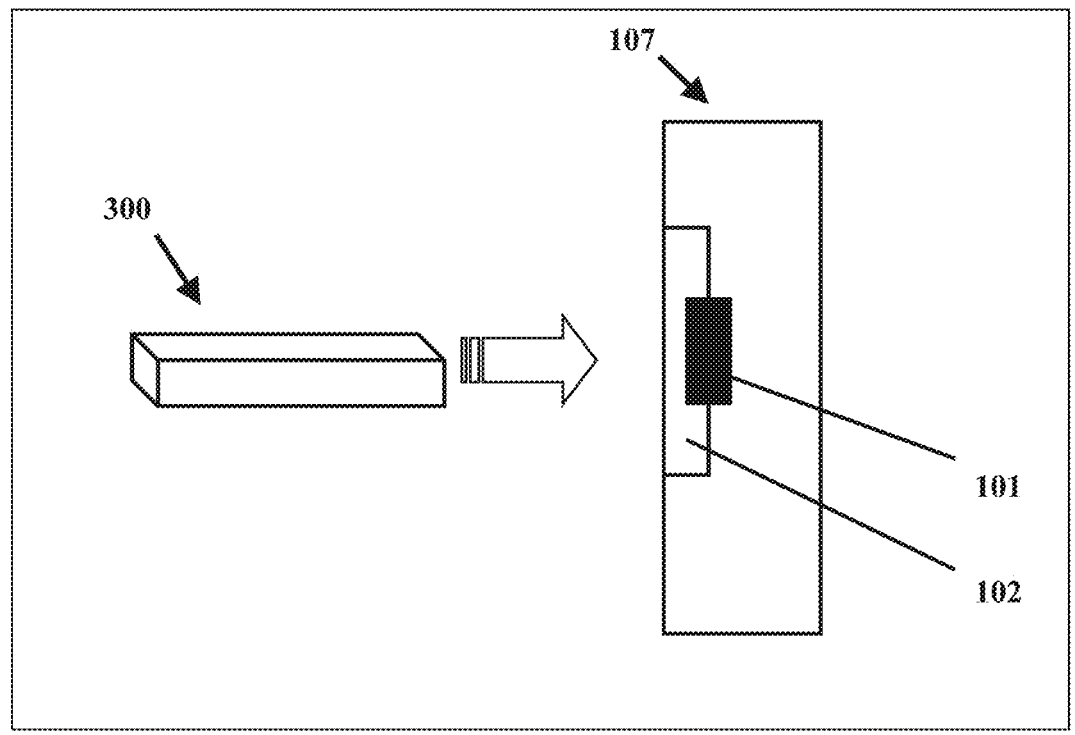
Figure 25B:
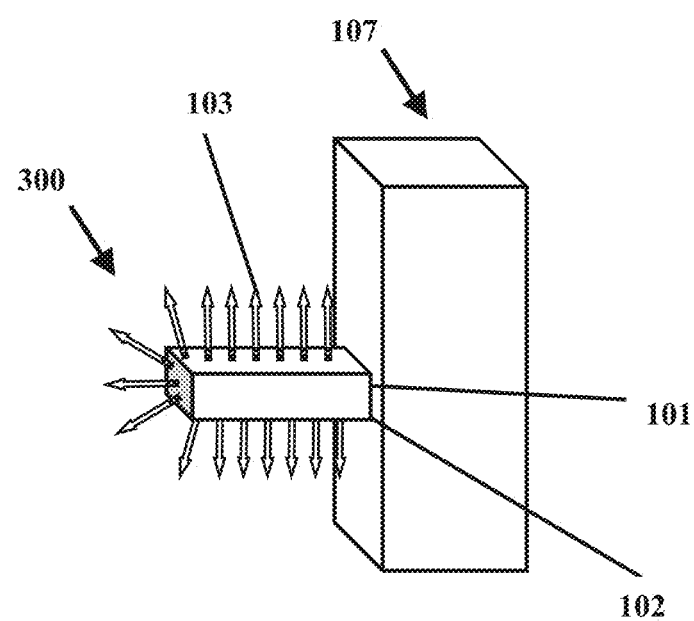
Figure 25C:
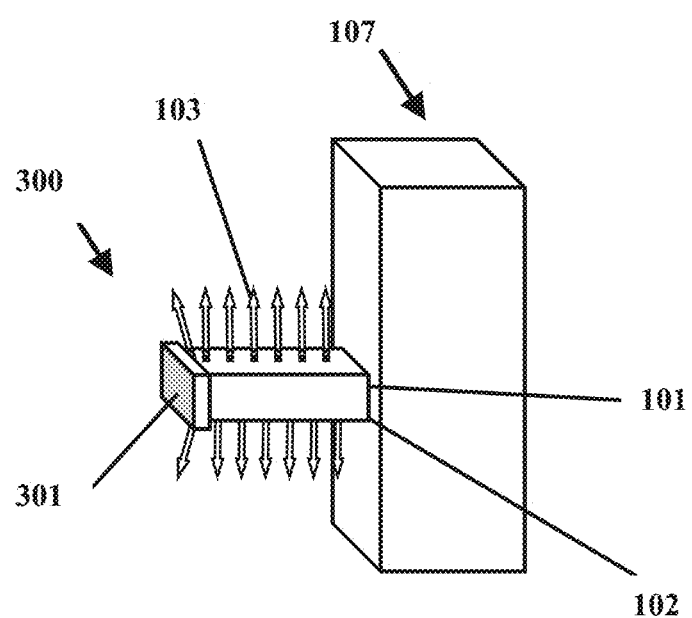

FIGS. 25A, 25B and 25C depict an elongated crystal to operate with a device emitting light in connection with a treatment protocol, in accordance with an embodiment of the invention.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods or materials similar or equivalent to those described herein, which could be used in the practice of the present invention. Indeed, the present invention is in no way limited to the methods or materials described.

The invention relates to methods, systems and devices that can be used for female genital skin reduction, improvement of skin tone and/or treatment, prevention, reduction in the likelihood of developing and/or reduction in the severity of female urinary incontinence. Among the benefits and advantages of the invention are that it involves methods, systems and devices that are non-invasive, require no anesthesia, and require no recovery time. The invention may also be useful in treating mild, moderate or severe incontinence. Additionally, the invention may also be useful for women regardless of their age, skin color or severity of symptoms of involuntary leaking of urine, whether mild, moderate or severe. The invention may be implemented with no hospitalization required. In various embodiments, it may be implemented as a low-risk, outpatient procedure. It may result in significant cost savings. In fact, the invention may eliminate the high costs and morbidity associated with the present surgical treatment options available for stress urinary incontinence.

When the pelvic floor muscles, connective tissue and skin of the female genitals are weakened by an increase of pressure on the pelvic muscles during pregnancy, or by maximal stretching of the pelvic tissues during childbearing, or by loss of estrogen effect on genital tissues after menopause, or by general laxity due to aging, the intrinsic (functional) urethral tone and extrinsic (structural) urethral position are affected which lead to urinary incontinence. Medical and surgical treatments for female urinary incontinence have focused on methods for improving either intrinsic urethral tone or extrinsic urethral tone. In various embodiments, the present invention may improve both intrinsic urethral tone and extrinsic urethral tone—a dual treatment function not previously achieved with a single treatment. Thus, the present invention may address both structural and functional deficits that cause urinary incontinence.

A functional urethra—one with optimal tone—forms an adequate seal to stop involuntary leaking of urine. When urethral support is compromised functionally, the tone of the urethra is not adequate to maintain a tight seal to stop urine from leaking under pressure, for instance when the bladder is full. In various embodiments, this functional deficit, decreased intrinsic urethral tone, may be corrected.

A structurally supported urethra is surrounded by pelvic floor muscles, connective tissue and skin structures that lend support for optimal positioning of the urethra. When urethral support is compromised structurally, the position of the urethra becomes mobile during movements, referred to as urethral hyper-mobility, and leaking occurs with coughing, sneezing, laughing and even walking. In various embodiments of the present invention, this structural deficit, decreased extrinsic urethral tone, may be corrected.

In various embodiments of the present invention, the problems related or inherent to surgical procedures may be minimized or avoided entirely, because the inventive method can be performed in a non-invasive manner; that is, i) no injection of foreign substances is necessary, ii) no anesthesia is necessary, iii) no urethral overcorrection or over tightening is necessary, iv) no urethral scarring or obstruction results, v) no risk of infection or hemorrhage are present, vi) no foreign body use is necessary, and vii) no cutting or significant trauma to the skin is necessary.

In an embodiment, the invention includes the use of a device that provides a light source for non-cosmetic and/or medical treatment. In an embodiment, the device is used for female genital skin reduction. In another embodiment, the device is used for improvement of skin tone. In another embodiment, the device is used for the treatment, prevention, reduction in the likelihood of developing and/or reduction in the severity of one or more forms of female urinary incontinence, including stress urinary incontinence, urge urinary incontinence, mixed urinary incontinence, and overflow incontinence. In still further embodiments, the device is used to achieve one or more of the following benefits: improvement in urinary holding capacity, improvement in urinary control, improvement in urethral tone, improvement in urethral position, improvement of involuntary leaking of urine, improvement of perineal scars, improvement of external hemorrhoids, improvement of rectal holding capacity, improvement of anterior vaginal wall tone and improvement of cystocele, improvement of posterior vaginal wall tone and improvement of rectocele, improvement of vulvar varicosities, improvement of pelvic muscle tone, improvement of skin condition and/or health. As used herein, "improvement" includes any clinical change for the better with respect to a condition. In another embodiment, the device is used for treatment of vaginal prolapse and/or the treatment of rectal prolapse.

Alternative embodiments of the invention include use of the device and methods of the invention as a "biologic" treatment either externally applied to skin and/or internally applied to tissues, for infrared light augmentation of biological healing responses. For example, the device and methods may be used in the treatment, prevention, reduction in the likelihood of developing and/or reduction in the severity of chronically inflamed tonsils, an enlarged uvula in the posterior pharynx, stomach ulcers, mouth lesions, dermatologic skin disorders such as psoriasis, eczema and chronic skin disorders, enlarged prostate, vocal cord polyps, nasal polyps, and the like.

As illustrated in FIGS. 23A and 23B, the device 107 may include a treatment window 102 through which light 103 is emitted from a light source 101. The treatment window 102 may be configured to be placed near or against the tissue or skin or other anatomical structure to be treated (a surface of which is collectively illustrated as 104). The light source 101 may be one from which the light 103 that emanates is infrared and/or the light source 101 may be a broadband spectrum light source. In an embodiment, the light source 101 has a spectrum of 700 to 1,800 nanometers, such that the emitted light 103 may penetrate only about 1-3 mm in skin depth during use. The light source 103 may be capable of controlling skin temperature. Indeed, treatments utilizing the light source 103 of the present invention may not be painful or require anesthesia, which is distinctly different from radiofrequency treatments, which can penetrate beyond 20 mm in skin depth and are frequently described by patients as being painful.

Examples of devices that may be particularly useful in connection with various embodiments of the invention are described in U.S. patent application publication Nos. 2005/0049658, titled "Method and System for Treatment of Post-Partum Abdominal Skin Redundancy or Laxity," and 2006/0052847, titled "System and Method for Heating Skin Using Light to Provide Tissue Treatment," each of which are incorporated by reference herein in their entirety, as though fully set forth. The TITAN device (available from Cutera, Inc.) may also be used, as may other deep dermal heating devices, which are contemplated by the present invention. It should also be appreciated that the present invention contemplates modifications to known light based devices in order to optimize the methods of the present invention.

With reference again to FIG. 23, a layer of gel 105 may be applied to the surface of the tissue or skin or other anatomical structure 104 to be treated prior to use of the device 107. As will be readily appreciated by those of skill in the art, any number of gels may be used in connection with alternate embodiments of the present invention. In one embodiment, the gel is a cooled ultrasound gel. Once the gel 105 is applied to the surface 104, the device may be placed against the surface 104 and used to deliver light 103 to the surface 104. Following use, the gel 105 may be wiped away. The process of applying gel 105, using the device 107, and wiping away the gel 105 may be repeated in connection with various embodiments of the present invention, as illustratively described below.

A layer of a composition 106 may also be applied to the surface of the tissue or skin or other anatomical structure 104 to be treated prior to use of the device 107. In those embodiments of the invention where the composition 106 is used, the composition 106 is first applied to the surface 104, followed by the gel 105, such that the composition 106 lies substantially between the surface 104 and the gel 105. Once the composition 106 and the gel 105 are applied to the surface 104, the device may be placed against the surface 104 and used to deliver light 103 to the surface 104. Following use, the composition 106 and gel 105 may be wiped away. The process of applying the composition 106, applying the gel 105, using the device 107, and wiping away the composition 106 and the gel 105 may be repeated in connection with various embodiments of the present invention, as illustratively described below. The composition 106 may be inert and may not be absorbable by the skin.

In an embodiment of the invention, the composition 106 is in the form of a powder. The powder may include one or more of the following ingredients in varying amounts: micronized zinc oxide, micronized titanium dioxide, pigmenting titanium dioxide, iron oxide, oat, rice, mica, silicone powder, marine algae and/or talc. As used herein, "micronized" describes a relatively small particle size (especially with regard to the particle size of like compounds used in traditional sunscreen products), which may be, for instance, in the range of about 30μ to about 50μ, and in certain embodiments, of about 40μ. As used herein, "pigmenting titanium dioxide" is a form of titanium dioxide with a relatively large particle size, which may be, for instance, at least 850μ, at least 900μ, at least 950μ and/or up to about 1,000μ. The composition 106 may be formulated to include particles of varying size so as to reflect, refract and/or scatter light exposed to it in a generally predetermined manner. Certain products useful as compositions 106 herein may be obtained from Colorescience (Dana Point, Calif.); for instance; its Sunforgettable Mineral Powder Sun Protection SPF 50 and its Pressed Illuminating Pearl Powder, alone or in combination.

The composition 106 may also include a quantity of salicylic acid, which may itself be in powder form. The salicylic acid powder may be of a range of concentrations, as will be readily appreciated by those of skill in the art, such as 0.01%, 0.05%, 0.1%, 0.5%, 1.0% 1.5%, 2.0%, 2.5% or 3.0%. In an embodiment of the present invention, the salicylic acid powder is 1% salicylic acid powder. In an alternate embodiment of the invention, particularly advantageous when treating hemorrhoid tissue or anal skin tags, the composition 106 is 2% salicylic acid powder.

Preparing the skin before each pass of infrared light with a powdered mineral preparation, such as the composition 106, before the application of cold gel, as described above, has clinically proven to augment the skin tightening effect, while advantageously cooling the surface of the skin through the inherent properties of minerals and mineral pigments, which are known to have a surface cooling effect.

In an alternate embodiment of the invention; as illustrated in FIGS. 25A and 25B, an adaptor 200 is provided. The adaptor 200 may be desirable to effectuate the treatment of areas of the body that are not fully exposed to the outside environment and/or that are not easily reachable without substantial manipulation of tissue for access. Thus, the adaptor 200 may be particularly useful when it is desirable to treat; for instance, the vaginal walls. Moreover, as will be apparent to those of skill in the art, there are numerous diseases or biological conditions that may be treated by use of the adaptor 200, and these are by no means limited to the fields of gynecology or regions of the female anatomy that have been discussed with respect to the present invention thus far. Indeed, regions and conditions within other body orifices can be treated through use of the adaptor 200, such as, but in no way limited to, internal hemorrhoids, chronically enlarged tonsils, enlarged prostate, nasal polyps and vocal chord polyps.

The adaptor 200 has a first end 204 and a second end 202 with a shaft 203 therebetween. An opening 201 is configured on the shaft 203. The shaft 202 may be generally cylindrical, and may have overall dimensions ranging from about 1 cm to about 20 cm in length, and from about 0.25 cm to about 3 cm in width. In an embodiment of the invention intended for the treatment of vaginal walls, the overall dimensions of the adaptor may be about 6.5 cm to about 8.5 cm in length (in one instance, about 7.5 cm in length), and about 0.5 cm to about 1.0 cm in width.

The shaft 203 is illustratively depicted as being generally cylindrical in FIGS. 24A and 24B, but any number of other configurations may be used in alternate embodiments of the invention, as will be readily appreciated by those of skill in the art. For instance, the shaft may have a conical shape (not shown) whereby the first end has a larger diameter and/or surface area than the second end. Moreover, the second end may be configured in any number of shapes to facilitate insertion of the adaptor into a body orifice safely and comfortably, and may be tailored for the particular application for which it is intended to be used and/or the body orifice into which it is intended to be inserted. For instance, it may be flat, rounded or conical. Generally speaking, the overall shape of the adaptor 200 may be configured to enable safe and comfortable insertion, manipulation and use thereof to reach areas of the body within various orifices as described above.

In an embodiment, the first end 204 is configured to mechanically interact with the device 107 such that, during operation, the emitted light 103 provided by light source 101 is expressed through the opening 201. Any number of mechanisms may be used internally within the shaft 203 to accomplish this. By way of example, a crystal (e.g., a sapphire crystal) may be included in the shaft 203 and in communication with the light source 101 such that operation of the light source 101 causes emitted light to reach the crystal (not shown), whereby it is transmitted and ultimately caused to emanate from the shaft 203 through opening 201. In such embodiments, the exterior surface of the shaft 203 is opaque, but for the opening 201 that permits the transmission of emitted light 103 therethrough. In another example, a series of one or more crystals, mirrors, prisms, lenses, or other reflective and/or refractive materials and/or assemblies may be included within shaft 203 to effectuate the transmission of emitted light 103 from the light source 101 through the opening 201.

The opening 201 is configured as a slit or other aperture that allows the internal elements of the adaptor 200 to have direct exposure to body tissues when in use. Alternatively, the opening 201 may include glass, plastic or another transparent or translucent material to avoid direct contact between the internal elements of the adaptor 200 and the body tissue being treated (similar to the treatment window 102 in the device 107).

The opening 201 depicted in FIGS. 24A and 24B is configured along the entire length of the shaft 203, but any number of other configurations may be used in connection with alternate embodiments of the invention. By way of example (not shown), the opening 201 may be configured along only a portion of the length of the shaft 203, it may be a series of one or more apertures (e.g., a series of holes of any shape), or it may be configured to wrap entirely around the shaft 203 for 360° application of light. The clinical goal may be to focus the light in the direction(s) of the regions specifically intended for treatment with that particular transmission of emitted light, and not to haphazardly or unevenly emit light within an orifice, Particularly with that clinical goal in mind, still further configurations will be apparent to those of skill in the art and are contemplated as being within the scope of the present invention.

Additionally, in alternate embodiments the opening 201 may be partially or fully located on the second end 202, so as to direct light axially from the adaptor 200, rather than in a generally radial direction. However, at least in certain embodiments, such as when the adaptor 200 is used to treat vaginal walls, the second end 202 is opaque so as to avoid damaging the cervix.

The adaptor 200 may be configured as a permanent, integrated element of the device 107, or it may be removable therefrom such that the device 107 can be used either with or without it. In another embodiment, the adaptor 200 can be rotated relative to the device 107 either while light is being emitted therefrom or between each in a series of applications of light therefrom, Rotation may be accomplished manually or automatically.

In yet another embodiment of the invention, as illustrated in FIGS. 25A and 25B, an elongated light source 300 is provided. The elongated light source 300 may be desirable to effectuate the treatment of areas of the body that are not fully exposed to the outside environment and/or that are not easily reachable without substantial manipulation of tissue for access, Thus, the elongated light source 300 may be particularly useful when it is desirable to treat, for instance, the vaginal walls. Moreover, as will be apparent to those of skill in the art, there are numerous diseases or biological conditions that may be treated by use of the elongated light source 300, and these are by no means limited to the fields of gynecology or regions of the female anatomy that have been discussed with respect to the present invention thus far. Indeed, regions and conditions within other body orifices can be treated through use of the elongated light source 300, such as, but in no way limited to, internal hemorrhoids, chronically enlarged tonsils, enlarged prostate, nasal polyps and vocal chord polyps.

The elongated light source 300 may be a crystal, such as a sapphire crystal. It may have overall dimensions ranging from about 1 cm to about 20 cm in length, and from about 0.25 cm to about 3 cm in width. In an embodiment of the invention intended for the treatment of vaginal walls, the overall dimensions of the elongated light source 300 may be about 6.5 cm to about 8.5 cm in length (in one instance, about 7.5 cm in length), and about 0.5 cm to about 1.0 cm in width, Generally speaking, the overall shape of the elongated light source 300 may be selected to enable safe and comfortable insertion, manipulation and use thereof to reach areas of the body within various orifices as described above, Its edges may be beveled or rounded to minimize any tissue pinching, irritation or trauma during use while being configured to be gently pressed against tissue during use.

In an embodiment, the elongated light source 300 is configured to mechanically interact with the device 107 such that, during operation, the emitted light 103 provided by light source 101 is expressed through the elongated light source 300.

Additionally, in alternate embodiments, as illustrated in FIG. 25C, a cap 301 may be included on the elongated light source 300 so that light emitted from the elongated light source 300 does not travel in an axial direction therefrom. This can be particularly advantageous in certain embodiments, such as when the elongated light source 300 is used to treat vaginal walls, and axial light emitted therefrom could damage the cervix. The cap 301 may be configured in any number of shapes to facilitate insertion of the elongated light source into a body orifice safely and comfortably, and may be tailored for the particular application for which it is intended to be used and/or the body orifice into which it is intended to be inserted. For instance, it may be flat, rounded or conical.

The elongated light source 300 may be configured as a permanent, integrated element of the device 107, or it may be removable therefrom such that the device 107 can be used either with or without it. In another embodiment, the elongated light source 300 can be rotated relative to the device 107 either while light is being emitted therefrom or between each in a series of applications of light therefrom. Rotation may be accomplished manually or automatically.

Figure 1:
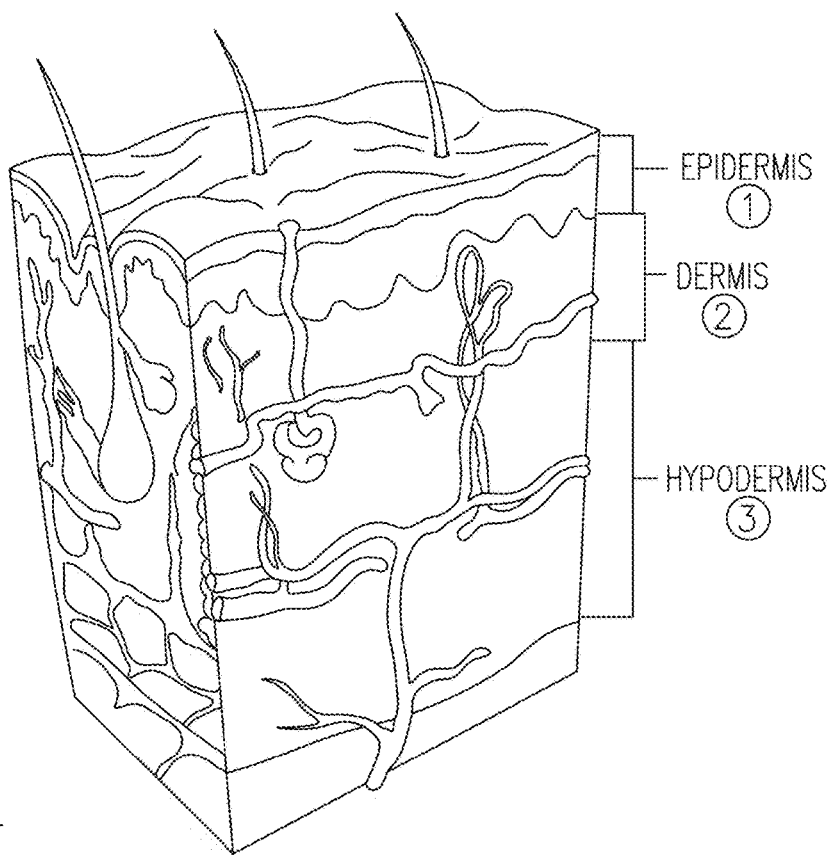
FIG. 1 (prior art) is a schematic illustration of the skin structure.

In an embodiment, the device is used to deliver infrared light and thereby heat the dermal layer of the skin (FIG. 1, #2). Sustained heating of the dermal layer of the skin over several seconds (e.g., up to six seconds, in one embodiment) contracts the collagen and elastin components of the dermis and/or causes long-term stimulation of collagen and elastin remodeling through fibroblast activity, resulting in tightening of skin, reduction of skin, and/or improved skin tone. Photographs taken before and after application of this technique appear as FIGS. 3-6 and 16-22.

Figure 2:
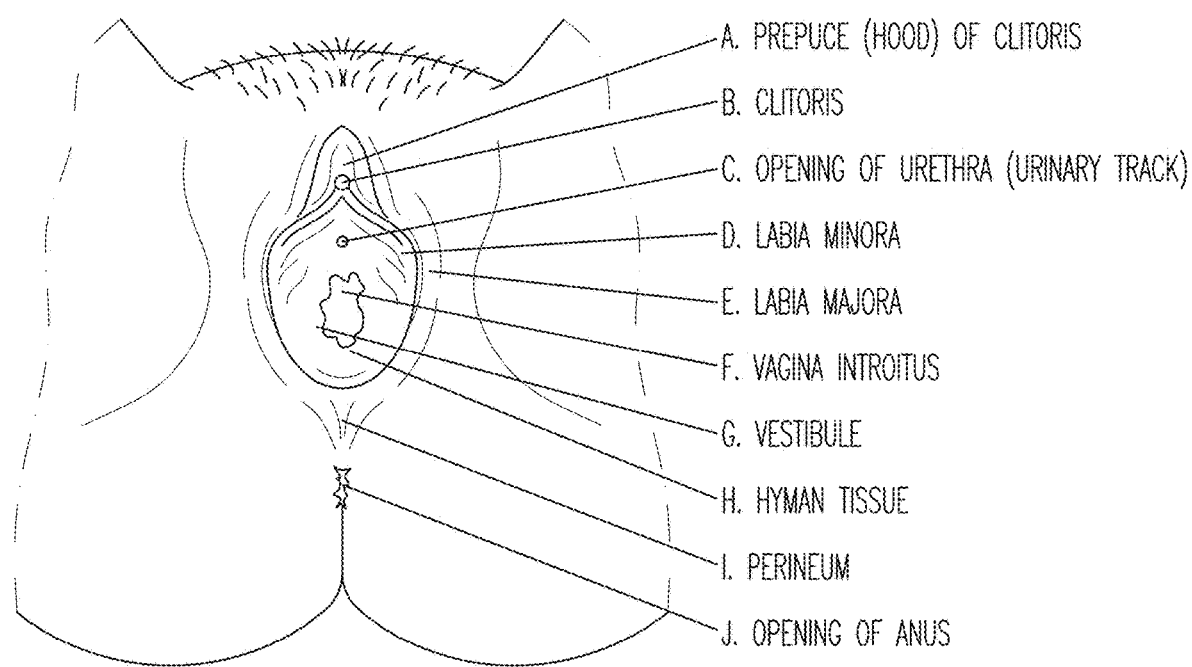
FIG. 2 (prior art) is a schematic illustration of the female genitalia.
Figure 3A:
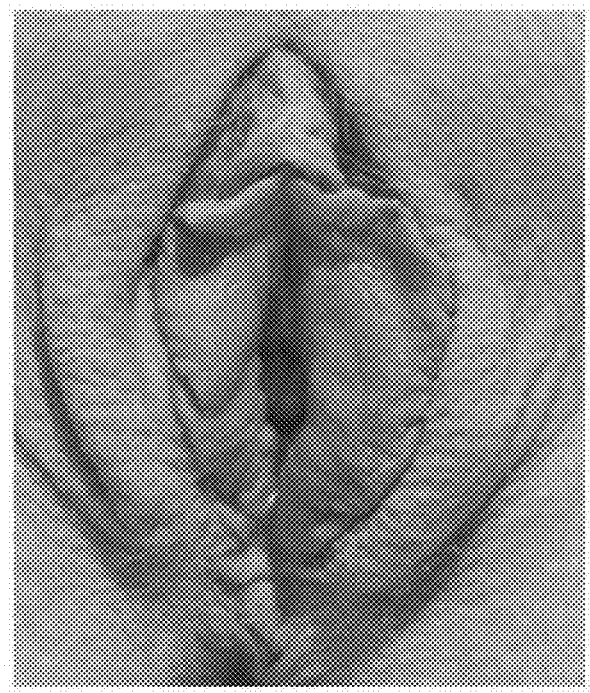
FIG. 3A is a photograph of female genitalia prior to treatment.
Figure 3B:
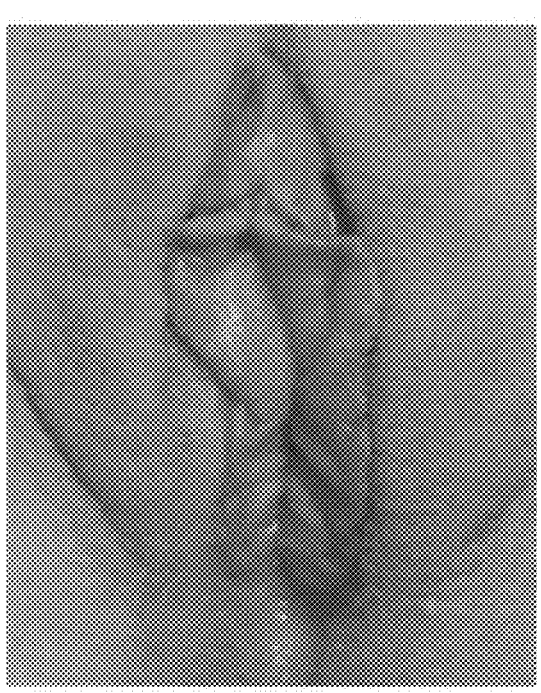
FIG. 3B is a photograph of the same female genitalia after treatment, illustrating reduction and toning in skin of labia majora, labia minora, clitoral hood and perineum in accordance with an embodiment of the present invention.

In connection with an embodiment of the invention, a procedure is performed using the device, to apply light to eight treatment areas; specifically, (i) the prepuce (hood) of the clitoris, (ii) the opening of the urethra (urinary tract) and periurethral tissues, (iii) labia minora, (iv) labia majora, (v) vagina introitus, (vi) perineum, (vii) opening of anus and (viii) vaginal walls (as illustrated in FIG. 2). One exemplary embodiment of the procedure involving each of these eight treatment areas is as follows. As those of skill in the art will readily appreciate, any number of variations to the following sequence of applications and treatment areas may be used in alternate embodiments of the invention, Simply by way of example, one or more treatment areas may not be included when the treatment is implemented, or the order in which the various treatment areas are addressed may be altered. Additionally, the composition may take a variety of forms or be eliminated altogether. Additionally, an adaptor and/or elongated light source may be used for one or more of each treatment area. The ensuing description is merely a description as to how the device may be implemented when used in connection with these particular treatment areas.

Application to Labia Majora

The device may be used to treat the labia majora (FIG. 2, E) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled. (post-cooling is optional) (As used herein, this is what is meant by a "pulse,") Next, pulses are continued with minimal overlapping until the treatment area has been covered. (As used herein, the series of pulses required to substantially cover a treatment area is referred to as a "pass".) Upon completion of a pass, the composition and gel are wiped away, replaced with a layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the labia majora is completed. Treatment of the labia majora may result in some immediate reduction in skin and ongoing reduction of skin over several weeks thereafter.

In one embodiment, the procedure can be used to reduce and tone skin of labia majora. This is illustrated in FIGS. 3, 4, 5 and 6. Among other things, in one embodiment the procedure may be used to preferentially reduce and tone skin more on one side of the treatment area than on the other side to improve labia majora symmetry for women who have significant size discrepancy between the two sides of the labia majora. In another embodiment, the procedure may be used to reduce vulvar varicosities. This is illustrated in FIG. 4.

Application to Labia Minora

The device may be used to treat the labia minora (FIG. 2, D) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled (optional). Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the labia minora is completed. Treatment of the labia minora may result in some immediate reduction in skin and ongoing reduction of skin over several weeks thereafter.

In one embodiment the procedure can be used to reduce and tone skin of labia minora. This is illustrated in FIGS. 3, 4, 5, 6, 16 and 17, Among other things, in one embodiment the procedure may be used to preferentially reduce and tone skin more on one side of the treatment area than on the other side to improve labia minora symmetry for women who have significant size discrepancy between the two sides of the labia minora.

Application to Prepuce (Hood) of Clitoris

The device may be used to treat the prepuce (hood) of the clitoris FIG. 2, A) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled (optional). Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the prepuce of the clitoris is completed. Treatment of the prepuce of the clitoris may result in some immediate reduction in skin and ongoing reduction of skin over several weeks thereafter.

In one embodiment the procedure can be used to reduce and tone skin of the clitoral hood. This is illustrated in FIGS. 3, 4, 5, 6, 16 and 17.

Application to Opening of the Urethra (Urinary Tract)

The device may be used to treat the periurethral and/or urethral skin (FIG. 2, C) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled (optional). Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which, unique for this treatment area, is a restriction to five or less passes, due to the limited size of this treatment area and acute response rate. Once the desired number of passes is completed, treatment of the opening of the urethra and periurethral tissues is completed. Treatment of the periurethral and/or urethral skin may result in some immediate reduction in skin and ongoing reduction of skin over several weeks thereafter.

In one embodiment the procedure can be used to reduce and tone skin of the urethra opening. This is illustrated in FIGS. 16, 17 and 18. Among other things, in one embodiment the procedure may be used to improve the urethral position. This is illustrated in FIGS. 16, 17 and 18.

Application to Vagina Introitus

The device may be used to treat the vagina introitus (FIG. 2, F) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled. Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the vagina introitus is completed. Treatment of the vagina introitus may result in some immediate reduction in skin and ongoing reduction of skin over several weeks thereafter.

In one embodiment the procedure can be used to reduce and tone skin of the vaginal introitus. This is illustrated in FIGS. 4, 6, 16, 17 and 18.

Application to Perineum

The device may be used to treat the perineum (FIG. 2, I) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled, Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the perineum is completed. Treatment of the perineum may result in some immediate reduction in skin and ongoing reduction of skin over several weeks thereafter.

In one embodiment the procedure can be used to reduce and tone skin of the perineum. This is illustrated in FIGS. 3, 4, 5 and 19. Among other things, in one embodiment the procedure can be used to improve perineal scarring. This is illustrated in FIG. 19, Application to Opening of Anus The device may be used to treat the opening of the anus (FIG. 2, J) just after a layer of a composition including micronized zinc oxide, micronized titanium dioxide, mica and 2% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled. Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the opening of the anus is completed.

In one embodiment the procedure can be used to reduce and tone skin of the anus. This is illustrated in FIGS. 4, 19, 21 and 22. In another embodiment, where the treatment of external hemorrhoids is desired, the aforementioned composition may be 2% salicylic acid powder (i.e., without the micronized zinc oxide, micronized titanium dioxide and mica). This is illustrated in FIG. 20. Among other things, in one embodiment the procedure can be used to treat rectal prolapse. This is illustrated in FIG. 22.

Application to Vaginal Walls

The device may be used to treat the vaginal walls (FIG. 2, above F) just after a layer of a composition including micronized zinc oxide, micronized titanium dioxide, mica and 1% salicylic acid powder is applied to the region, and then cooled ultrasound gel is applied atop the composition. When the treatment window is placed firmly onto the skin, the pulse is started. Within the span of several seconds the skin is pre-cooled, heated with infrared light and post-cooled (optional). Next, pulses are continued with minimal overlapping until the treatment area has been covered. Upon completion of a pass, the composition and gel are wiped away, replaced with new layers of composition and gel over the treatment area, and the area is again covered in pulses to complete a pass. This process continues for the desirable number of passes, which can be readily determined in each instance by a skilled artisan, based on a variety of factors, such as, but not limited to, the condition of the treatment area before treatment and the response of the treatment area to one or more passes. Once the desired number of passes is completed, treatment of the vaginal walls is completed.

In one embodiment the procedure can be used to reduce and tone skin the vaginal walls. This is illustrated in FIGS. 4, 6, 16 and 17. In another embodiment the procedure can be used to reduce and tone skin of the anterior vaginal sidewalls for improvement of cystocele. This is illustrated in FIGS. 4, 6, 16 and 17. In yet another embodiment the procedure can be used to reduce and tone skin of the posterior vaginal sidewalls for improvement of rectocele. This is illustrated in FIG. 6. Among other things, in one embodiment, this procedure can be used to treat vaginal vault prolapse for improvement of cystocele and rectocele. This is illustrated in FIG. 6.

Example #1: Treatment of Stress and Mixed Urinary Incontinence

One application of a method of the present invention encompasses the following six treatments: labia majora reduction; labia minora reduction; clitoral hood reduction; periurethral reduction; vaginal introitus reduction and perineal reduction. Implementing all six of these treatment areas collectively may be used to treat stress urinary incontinence ("SUI"). The treatments performed on the six areas listed above are usually performed in the order listed, but may nonetheless be effective if performed in no particular order. It is the collective reduction of the six areas of the female external genitalia that results in treatment of the symptoms of SUI, in connection with this example.

The number of treatments needed to treat symptoms of SUI to the patient's satisfaction will vary according to the severity of the symptoms, age of the patient and the degree of laxity. The treatments typically take approximately 75 minutes to perform. Repeat treatments may be performed as soon as the next calendar day, but preferably two weeks apart.

Some patients' treatment response to methods of the present invention is dramatic and can result in rapid improvement of SUI symptoms. Younger patients with younger collagen and elastin tend to achieve faster reduction of treatment areas and more rapid improvement of SUI symptoms. Older patients, who often have a higher severity of SUI symptoms, older collagen and elastin and more laxity, tend to have slower reduction of treatment areas and achieve slower but ongoing improvement of SUI symptoms with treatments in series.

In patients who undergo multiple treatments in series for ongoing treatment of their SUI symptoms, the treatment protocol may be modified over time according to the anatomic assessment of the provider. The following areas are excluded from the treatment protocol once optimal visible reduction is achieved: the labia majora area, the labia minora area, and the clitoral hood area. As optimal visible reduction is achieved of these three areas, the method can be modified to include only treatment using the standard protocol for periurethral area reduction and using a modified protocol for vaginal introitus area reduction using passes on the superior aspect of the vaginal introitus which improves inferior tissue support for the urethra, and passes on the lateral and inferior vaginal introitus as needed for laxity treatment.

The method utilizes a broadband light based device (700 nm-1,800 nm) that performs deep dermal heating, for example, the TITAN device (available from Cutera, Inc.).

FIG. 7 is a flow chart 10 for implementing this exemplary method of the present invention. The method is performed in the following order at block 12 labia majora reduction occurs. At block 14—labia minora reduction. Clitoral hood reduction is performed next as shown by block 16. At block 18—periurethral reduction. In blocks 20 and 22, vaginal introitus reduction and perineal reduction, respectively. In blocks 24 and 26, anal reduction and vaginal wall reduction, respectively. Each of the separate procedures will be described in detail below separately. It should be appreciated that the mechanical operation of the light based device is known and will not be discussed in detail.

At block 12 reductions of the labia majora are performed by placing a patient in the dorsal lithotomy position on an examining table with stirrups designed for gynecologic examinations. Next, using current medical guidelines from the American College of Obstetricians and Gynecologists for positioning a female patient for a gynecologic exam, the patient is positioned for optimal visualization of the treatment area, guiding the knees apart and the pelvis superiorly as needed. Begin with either the left labia majora or the right labia majora. The side chosen to be treated first is designated as side A. With gloved hands skin is lightly coated with mineral powder and a generous amount (approx. ¼ inch thick) of cool ultrasound gel that has been stored in the refrigerator is applied to the side of the labia majora being treated, side A. Referring to block diagram 30 of FIG. 8, at block 32, using an approximate setting of 30-55 Joules/cm2 (noting that fluences vary with individual infrared devices), place the heating device (not shown), for example, a sapphire crystal, directly against the skin of the labia majora while applying moderate pressure. The heating device can be positioned either horizontally or vertically, though this orientation should be continued throughout the treatment of the labia majora. At block 34, the foot pedal, hand trigger or other actuating mechanism of the device (not shown) is depressed to begin the pulse of energy while continuing direct application of the device to the skin for the duration of the pulse (approximately six to eight seconds). The total amount of time is adjustable and encompasses a range of time, thus the present invention should not be limited to a specific time amount.

Next, as shown in block 36, the device is re-placed directly below or beside the area just treated with minimal overlap of the previously directed pulse. Again, in block 38, the foot pedal, hand trigger or other actuating mechanism is depressed to begin the approximately six to eight second pulse of energy (see above) while continuing skin contact with moderate pressure applied throughout the duration of the pulse. The skin of the entire treatment area is treated with moderate overlap of the preceding pulse until the entire treatment area has been treated. Steps 36 and 38 are repeated until the entire area has been covered with a pulse, this is referred to as a completed 'pass'. At block 40 when one pass of the treatment area, side A, is completed, "yes," the device is used to treat side B. At this time, the used gel is wiped away and disposed, for example, the used gel can be wiped onto a disposable medical blue pad.

In preparation for treatment indicated by block 42, approximately ¼ inch of cool gel is applied to the opposite side, side B, of the treatment area as described above and using the exact protocol outlined above another series of pulses with minimal overlapping of the individual pulses to complete the first pass on the opposite side of the labia majora occurs. When the first pass is complete on the opposite side, side B, of the treatment area the used gel is wiped off and disposed of. For example, as shown in block 44, additional passes of both side A and side B can be done exactly as described above with passes over the both sides of the Labia majora in this treatment area. It should be appreciated that the present invention contemplates a range in the number of passes the provider may take on the treatment area and hence should not be limited by a specific number of passes.

If discrepancy in size of the two labia majora is observed by the provider, the asymmetry can be treated by reducing the total passes performed on the smaller labia majora depending on the extent of the size discrepancy. Next, the larger labia majora can be fully treated with standard protocol of passes.

Referring again to FIG. 7, at block 14 reduction of the labia minora is implemented. As with the labia majora reduction described above, the procedure begins by placing a patient in the dorsal lithotomy position on an examining table with stirrups designed for gynecologic examinations. Next, using current medical guidelines from the American College of Obstetricians and Gynecologists for positioning a female patient for a gynecologic exam, the patient is positioned for optimal visualization of the treatment area, guiding the knees apart and the pelvis superiorly as needed.

Begin with either the left labia minora or the right labia minora. The side chosen to be treated first is designated as side A. With gloved hands, mineral powder is lightly applied to area followed by a generous amount (approx. ¼ inch thick) of cool ultrasound gel that has been stored in the refrigerator is applied to the side of the labia majora being treated, side A. Referring to block diagram 50 of FIG. 9, at block 52, using the setting of 30-55 Joules/cm2, place the heating device (not shown), for example, a sapphire crystal, directly against the skin of the labia minora while applying moderate pressure. The heating device can be positioned either horizontally or vertically, though this orientation should be continued throughout the treatment of the labia minora. At block 54, the foot pedal, hand trigger or other actuating mechanism of the device (not shown) is depressed to begin the pulse of energy while continuing direct application of the device to the skin for the duration of the pulse (approximately six to eight seconds). The total amount of time is adjustable and encompasses a range of time, thus the present invention should not be limited to a specific time amount.

Next, as shown in block 56, the device is replaced directly below or beside the area just treated with minimal overlap of the previously directed pulse. Again, in block 58, the foot pedal, hand trigger or other actuating mechanism is depressed to begin the approximately six to eight second pulse of energy (see above) while continuing skin contact with moderate pressure applied throughout the duration of the pulse. The skin of the entire treatment area is treated with moderate overlap of the preceding pulse until the entire treatment area has been treated. Steps 56 and 58 are repeated until the entire area has been covered with a pulse (i.e., a completed "pass"). At block 60 when one pass of the treatment area, side A, is completed, "yes," the device is used to treat side B. At this time, the used gel is wiped away and disposed, for example, the used gel can be wiped onto a disposable medical blue pad.

In preparation for treatment indicated by block 62, mineral powder and approximately ¼ inch of cool gel is applied to the opposite side, side B, of the treatment area as described above and using the exact protocol outlined above another series of pulses with minimal overlapping of the individual pulses to complete the first pass on the opposite side of the labia minora occurs. When the first pass is complete on the opposite side, side B, of the treatment area the used gel is wiped off and disposed of. For example, as shown in block 64, additional passes of both side A and side B can be done exactly as described above, for multiple passes over the both sides of the labia minora in this treatment area. It should be appreciated that the present invention contemplates a range in the number of passes the provider may take on the treatment area and hence should not be limited by a specific number of passes.

When discrepancy in size of the two labia minora is observed by the provider, the asymmetry is treated by reducing the total passes performed on the smaller labia minora depending on the extent of the size discrepancy. Next, the larger labia minora can be fully treated with standard number of passes.

Referring again to FIG. 7, in block 16, clitoral hood reduction is the next step in the implementation of the present invention. As in the other treatment protocols, the patient is placed in the dorsal lithotomy position on an examining table with stirrups designed for gynecologic examinations. Next, the patient is positioned for optimal visualization of the treatment area guiding the knees apart and the pelvis superiorly as needed. Beginning superiorly over the clitoral hood, with gloved hands mineral powder is applied and a generous amount (approx. ¼ inch thick) of cool ultrasound gel that has been refrigerated is applied to the area above the clitoris and laterally on either side of the clitoris.

As shown in FIG. 10, block diagram 70 illustrates the implementation of the method steps for clitoral reduction. At block 72, using the setting of 30-55 Joules/cm2, the device, for example, a sapphire crystal is placed directly against the skin of above the clitoral hood while applying moderate pressure. The device should be orientated horizontally when treating the area above the clitoris. At block 74, the foot pedal, hand trigger or other actuating mechanism of the device (not shown) is depressed to begin the pulse of energy while continuing direct application of the device to the skin for the duration of the pulse (approximately six to eight seconds). The total amount of time is adjustable and encompasses a range of time, thus the present invention should not be limited to a specific time amount.

In block 76 treatment of the skin of the upper clitoral hood treatment area is continued with moderate overlap of the preceding pulse until the upper clitoral hood treatment area is completed. Next, as illustrated in block 78 and 80 the heating device is orientated vertically and used to treat the area on either side of the clitoral hood as described above. Steps 72-80 are repeated until the entire lateral clitoral hood treatment area and the upper clitoral hood treatment area has been covered with a pulse (i.e., a completed "pass"). When one pass of the treatment area is completed as shown in block 82, the used gel can be wiped away gently in a downward direction because of tissue proximity to the sensitive clitoral opening. Mineral powder and approximately ¼ inch of cool gel is reapplied to the treatment area as described above and using the exact protocol outlined above, another series of pulses over the clitoral hood treatment area is implemented as described above.

Block 84 can be repeated, for example, for three more passes exactly as described above, for a total of five passes over this clitoral hood treatment area. It should be appreciated that the present invention contemplates a range in the number of passes the provider may take on the treatment area and hence should not be limited by a specific number of passes.

As shown by block 18 of FIG. 7, the method of the present invention provides a protocol for reducing the urethral opening and the periurethral anatomy. The patient is placed in the dorsal lithotomy position and/or McRoberts position on an examining table with stirrups designed for gynecologic examinations and positioned for optimal visualization of the treatment area. Beginning with the skin superior to the urethral opening and inferior to the clitoris mineral powder and a generous amount (approx. ¼ inch thick) of refrigerated ultrasound gel is applied to the area above the urethral opening.

Referring to FIG. 11, in block diagram 90, using the setting of, for example, 30-55 Joules/cm2, in step 92, the heating device, for example, a sapphire crystal, is placed directly against the skin superior to the urethral opening while applying moderate pressure. The device can be orientated either horizontally or vertically. Typically a horizontal orientation works well beginning superior to the urethra and continuing below the urethra entering the superior vagina to treat the inferior aspect of the urethra for full coverage of the treatment area.

In step 94, a pulse of energy is applied while continuing direct application of the device to the skin for the duration of the pulse (approx. six to eight seconds). Next, at step 96 the device is repositioned directly below or beside the area just treated with minimal overlap of the previously directed pulse. Again at step 98, the foot pedal, hand trigger or other actuating mechanism is depressed to begin the approx. six to eight second pulse of energy while continuing skin contact with moderate pressure applied throughout the duration of the pulse.

Continue treating the skin of the entire treatment area with moderate overlap of the preceding pulse until the entire treatment area has been treated. Steps 96 and 98 are repeated until the entire area has been covered with a pulse (i.e., a completed "pass") shown in step 100. When one pass of the periurethral treatment area is completed, the used gel is wiped away and disposed of. Mineral powder and gel can be reapplied to the treatment area as described above and using the exact protocol outlined above, begin another series of pulses with minimal overlapping of the individual pulses to complete the second pass of the periurethral area as shown by block 100. As indicated in step 102 the above can be repeated as desired with a maximum of five passes over the periurethral treatment area.

As shown in FIG. 7, the next recommended treatment step according to this exemplary method of the invention is vaginal introitus reduction indicated by block 20. The patient is placed in the dorsal lithotomy position and/or McRoberts position on an examining table with stirrups designed for gynecologic examinations and positioned for optimal visualization of the treatment area.

Beginning at one side of the vaginal introitus and continuing circumferentially, horizontally or vertically, mineral powder and a generous amount (approx. ¼ inch thick) of refrigerated ultrasound gel is applied to the vaginal introitus area.

As shown in FIG. 12, in block diagram 110, using a setting of for example, 30-55 Joules/cm2, the heating device is placed directly against the skin on one side of the vaginal opening at the hymenal ring and moderate pressure is applied at step 112. The heating device can be orientated horizontally and directed inside the hymenal opening. This orientation should be continued when treating the inner hymenal area of the vaginal opening.

In step 114, a pulse of energy is applied while continuing direct application of the device to the skin for the duration of the pulse (approx. six to eight seconds). Next, at step 116 the device is repositioned directly below or beside the area just treated with minimal overlap of the previously directed pulse. Again at step 118, approximately six to eight second pulse of energy is applied while continuing skin contact with moderate pressure applied throughout the duration of the pulse.

As indicated treatment of the skin of the entire vaginal opening area with moderate overlap is continued by overlap of the preceding pulse until the entire vaginal opening treatment area has been treated. Next treat any skin in the vaginal opening treatment area not covered in the labia minora treatment protocol as shown by block 120. When one pass of the vaginal introitus treatment area is completed, the steps are repeated until the entire area has been covered with a pulse (i.e., a completed "pass") shown in step 122. When one pass of the area is completed, the used gel is wiped away and disposed of. Mineral powder and gel can be reapplied to the treatment area as described above and using the exact protocol outlined above, begin another series of pulses with minimal overlapping of the individual pulses to complete the second pass of the vaginal introitus area as shown by block 122. As indicated in step 124 the above can be repeated for multiple passes over the treatment area.

The remaining treatment area of according to the method of the present invention is perineal reduction as indicated by block 22 of FIG. 7. As with the previous treatment areas the patient is placed in the dorsal lithotomy and/or McRoberts position on an examining table with stirrups designed for gynecologic examinations and positioned for optimal visualization of the treatment area. Beginning with the skin below the vaginal introitus and above the anus, known as the perineum, mineral powder and a generous amount (approx. ¼ inch thick) of refrigerated ultrasound gel is applied to the perineum.

As shown in FIG. 13, in block diagram 130, using a setting of for example, 30-55 Joules/cm2, the heating device is placed directly against the skin of the perineum while applying moderate pressure in step 132. The device can be orientated either horizontally or vertically throughout the treatment pass. In step 134, a pulse of energy is applied while continuing direct application of the device to the skin for the duration of the pulse (approx, six to eight seconds). Next, at step 136 the device is repositioned directly below or beside the area just treated with minimal overlap of the previously directed pulse. It is acceptable to include the skin above and lateral to the anal area in this treatment area if visible laxity is present.

Again at step 138, approximately six to eight second pulse of energy is applied while continuing skin contact with moderate pressure applied throughout the duration of the pulse. As indicated treatment of the skin of the area with moderate overlap is continued by overlap of the preceding pulse until the entire treatment area has been treated. When the entire area has been covered with a pulse, this is referred to as a completed pass shown at 140.

When one pass of the area is completed, the used gel is wiped away and disposed of. Mineral powder and gel can be reapplied gel to the treatment area as described above and using the exact protocol outlined above, begin another series of pulses with minimal overlapping of the individual pulses to complete the second pass of the area as shown by block 142. As indicated, the above can be repeated to complete multiple passes over the treatment area.

Accordingly, due to the methodology of the present invention SUI can be treated by the collective reduction of six anatomical areas of the female external genitalia; that is, the labia majora area, the labia minora area, the clitoral hood area, the periurethral area, the vaginal introitus area, and the perineal area. For each of the six anatomical areas treated in the method there is a standard procedure that is unique to that area.

As set forth above, one to all six anatomical areas can be treated based upon a provider's clinical assessment of which anatomical areas would benefit from treatment. The exemplary method can also be modified slightly to treat labia minora asymmetry. The exemplary method can effectively treat discrepancy in size of the labia minora thereby restoring symmetry in the size of the labia minora. The protocol of the exemplary method can be modified to reduce the size of one side of the labia minora compared to the opposite side for treatment of asymmetry.

The exemplary method of the present invention is modified slightly to treat labia majora asymmetry. The exemplary method can treat discrepancy in size of the labia majora restoring symmetry in the size of the labia majora. The exemplary method can be modified to reduce the size of one side of the labia majora compared to the opposite side for treatment of asymmetry.

The exemplary method of the present invention can also be used to improve vulvar varicosities. The exemplary method can be used to reduce and tone the labia majora skin which improves support for underlying varicosities.

The exemplary method of the present invention can also be used to treat perineal scars. Using the exemplary method of perineal reduction, a perineal scar can be treated for improved function or comfort in the case of contracted perineal scars which are painful in certain seated positions or when a tampon insertion is attempted.

Example #2: Treatment of Anal Incontinence and Rectal Prolapse

Using the methodology of the present invention anal incontinence and rectal prolapse can be treated by the reduction of a seventh anatomical area of the female external genitalia; that is, the anal and peri-anal area. There is a standard procedure that is unique to this area.

At block 24 reductions of the anus and peri-anal tissues are performed by placing a patient in the dorsal lithotomy position followed by McRoberts position on an examining table with stirrups designed for gynecologic examinations. Next, using current medical guidelines from the American College of Obstetricians and Gynecologists for positioning a female patient for a gynecologic exam, the patient is positioned for optimal visualization of the treatment area, guiding the knees apart and the pelvis superiorly using a wedge lift as needed. Begin laterally on either side of the anus and include all peri-anal skin inferior to the coccyx. With gloved hands skin is lightly coated with mineral powder and a generous amount (approx. ¼ inch thick) of cool ultrasound gel that has been stored in the refrigerator is applied to the side A. Referring to block diagram 150 of FIG. 14, at block 152, using an approximate setting of 24-40 Joules/cm2, place the heating device (not shown), for example, a sapphire crystal, directly against the skin of the anal and peri-anal tissue while applying moderate pressure. The heating device can be positioned either horizontally or vertically. At block 154, the foot pedal or hand trigger or other actuating mechanism of the device (not shown) is depressed to begin the pulse of energy while continuing direct application of the device to the skin for the duration of the pulse (approximately six to eight seconds). The total amount of time is adjustable and encompasses a range of time, thus the present invention should not be limited to a specific time amount.

Next, as shown in block 156, the device is re-placed directly below or beside the area just treated with minimal overlap of the previously directed pulse. Again, in block 158, the foot pedal or hand trigger or other actuating mechanism is depressed to begin the approximately six to eight second pulse of energy (see above) while continuing skin contact with moderate pressure applied throughout the duration of the pulse. The skin of the entire treatment area is treated with moderate overlap of the preceding pulse until the entire treatment area has been treated. Steps 156 and 158 are repeated until the entire area has been covered with a pulse, this is referred to as a completed 'pass'.

When one pass of the area is completed, the used gel is wiped away and disposed of. Mineral powder and gel can be reapplied gel to the treatment area as described above and using the exact protocol outlined above, begin another series of pulses with minimal overlapping of the individual pulses to complete the second pass of the area as shown by block 150. As indicated, the above can be repeated to complete multiple passes over the treatment area.

The exemplary method of the present invention can be used to improve anal tone. Using the exemplary method of anal reduction, the anal and peri-anal areas can be treated for improvement of anal incontinence and treatment of rectal prolapse.

Example #3: Treatment of Vaginal Wall/Vaginal Vault Prolapse

Using the methodology of the present invention vaginal wall prolapse and vaginal vault prolapse can be treated by the reduction of an eighth anatomical area of the female genitalia; that is, the vaginal walls, There is a standard procedure that is unique to this area.

At block 26 reductions of the vaginal walls are performed by placing a patient in the dorsal lithotomy position followed by McRoberts position on an examining table with stirrups designed for gynecologic examinations. Next, using current medical guidelines from the American College of Obstetricians and Gynecologists for positioning a female patient for a gynecologic exam, the patient is positioned for optimal visualization of the treatment area, guiding the knees apart and the pelvis superiorly as needed. Begin treatment at any location within the vaginal vault, continuing circumferentially 360 degrees to complete one full pass. With gloved hands skin is lightly coated with mineral powder and a generous amount (approx. ¼ inch thick) of cool ultrasound gel that has been stored in the refrigerator to the skin of the vaginal wall. Referring to block diagram 170 of FIG. 15, at block 172, using an approximate setting of 45-60 Joules/cm2, place the heating device (not shown), for example, a sapphire crystal, directly against the skin of the vaginal wall tissue while applying moderate pressure. The heating device can be positioned either horizontally or vertically when using a shorter crystal, or the length of the crystal can be inserted into the vagina if using a customized adaptor. At block 174, the foot pedal or hand trigger or other actuating mechanism of the device (not shown) is depressed to begin the pulse of energy while continuing direct application of the device to the skin for the duration of the pulse (approximately six to eight seconds). The total amount of time is adjustable and encompasses a range of time, thus the present invention should not be limited to a specific time amount.

Next, as shown in block 176, the device is re-placed directly above, below or beside the area just treated with minimal overlap of the previously directed pulse. Again, in block 178, the foot pedal or hand trigger or other actuating mechanism is depressed to begin the approximately six to eight second pulse of energy (see above) while continuing skin contact with moderate pressure applied throughout the duration of the pulse. The skin of the entire treatment area is treated with moderate overlap of the preceding pulse until the entire treatment area has been treated. Steps 176 and 178 are repeated until the entire area has been covered with a pulse, this is referred to as a completed 'pass'.

When one pass of the area is completed, the used gel is wiped away and disposed of. Mineral powder and gel can be reapplied gel to the treatment area as described above and using the exact protocol outlined above, begin another series of pulses with minimal overlapping of the individual pulses to complete the second pass of the area as shown by block 170. As indicated, the above can be repeated to complete multiple passes over the treatment area.

The exemplary method of the present invention can also be used to treat vaginal wall prolapse and vaginal vault prolapse. Using the exemplary method of vaginal wall reduction, the anterior or superior vaginal wall can be treated for improvement of cystocele. Using the exemplary method of vaginal wall reduction, the posterior or inferior vaginal wall can be treated for improvement of rectocele.

Example #4: Pilot Study

Thirty women with urinary incontinence ("UI"), average age 43, volunteered to undergo genital infrared light therapy. Patients underwent three treatments of the device in dorsal lithotomy position using an average of 65 pulses of the device in each of 5 genital areas (i.e., labia majora, labia minora, urethral and peri-urethral, vaginal introitus and perineum). At 3 months post treatment, patients reported an average 83.1% UI improvement (from longer holding capacity to less volume leak and decreased pad use), reduced urethral hypermobility ("UH"), and improved ability to perform pelvic muscle (Kegel) exercises. At 16-24-month follow-up, 70.83% overall UI improvement was retained; patients performing Kegels regularly retained nearly all of their original treatment benefits (98.5%).

Pilot data suggested that the procedure was safe and effective. All women regardless of UI severity experienced some level of UI-mitigating response following tightening and toning of the urethra and surrounding tissues. Findings of the pilot treatment protocol provided insight into criteria for the characterization of success in UI improvement using this procedure.

Example #5: Clinical Study

Study Design, Eligibility

A prospective, controlled, nonequivalent-groups design was conducted. Female patients suffering from long-term UI were offered the option of participating in the clinical trial. Control group ("CG") patients were informed that they were participating in a controlled study, and that they would receive standard or placebo/sham treatment. Potential risks/duration of symptoms that might be experienced were explained to patients in both the CG and the treatment group ("TG").

Device Used in Study Infrared light treatment ("ILT") equipment used in the study was associated with a well-established safety record and had been Food and Drug Association (FDA) approved; specifically, the TITAN device (obtained from Cutera, Inc., Brisbane, Calif.). The device's light spectrum was 1100-1800 nm (output of 30-65 Joules/cm2), heating at depths of 1-3 mm. The epidermis was cooled to <40° for protection before, during, and following the procedure.

Treatment Protocol

Seven areas were treated in the TG: labia majora, labia minora, clitoral hood, urethral/peri-urethral area, vaginal introitus, perineum, and rectal area. Dorsal lithotomy and McRoberts positions were used to achieve adequate exposure. In the CG, the lowest heat setting (5 Joules/cm2, 20 pulses per treatment) on the device was used with a single pass over 6 treatment areas; heating directly over the urethra/peri-urethral area was strictly avoided. Table 1 presents the TG and CG protocol for number of procedures, intensity setting, treatment areas, ILT passes, as well as light pulses per procedure, procedures per patient, and days between procedures.

TABLE 1

| Comparison of treatment and control protocols | | |
|---|---|---|
| Variable | Treatment Group (n = 98) | Control Group (n = 10) |
| Total no. procedures | 207 | 30* |
| Light-energy intensity setting | 32 Joules/cm$^2$ | 5 Joules/cm$^{2\dagger}$ |
| No. treatment areas/No. of passes with light-energy device | 7/5 passes each | 4/1 pass (total avoidance of urethra) |
| Pulses per procedure, mean ± SD (range) | 108.7 ± 20.4 (36.0-160.0) | 20.1 ± 1.4 (18-23) |
| Procedures per patient, mean ± SD (range) | 2.1 ± 0.9 (1.0-4.0) | 3.0 ± 0.0 (3-3) |
| Days between procedures, mean ± SD (range) | 18.1 ± 23.1 (0.0-125.0) | 1.8 ± 0.7 (1-3) |

SD, standard deviation.
*Sham procedures
$^\dagger$Lowest possible energy setting on light-energy device Follow-Up Program Following treatments, the recommendation was made to perform Kegels for lifetime maintenance of treatment benefits.

Safety Endpoints

The primary safety endpoint was incidence of adverse events during or immediately following a treatment, including but not limited to burning, pain, or swelling at the treatment locations.

Efficacy Variables, Data Collection

Primary effectiveness variables (designation of having achieved "success threshold") were: % UI improvement, % UH, and ability to perform Kegels. Secondary effectiveness variables were: UI severity, UI in activity, pad usage, and improvement in holding capacity, control, treatment area support, skin laxity, and sensation. Measures of UI improvement were based on patient reporting. Change in UH was documented at examination by the physician. Skin laxity was assessed at each examination and recorded photographically. Concurrent diagnoses (e.g., cystocele, rectocele, rectal holding, hemorrhoid) were also noted and tracked. Data were collected at baseline, first follow-up (1-3 months after last treatment), and second follow-up (1-16 months after last treatment).

Statistical Analysis

The SPSS® software package (version 17, SPSS [IBM], Chicago, Ill.) was used to perform all statistical analyses. Statistical significance was set at $p<0.05$, Continuous demographic variables were reported as mean, standard deviation (SD), and range; categorical demographic variables were reported as number and percentage. Complications were also reported as number and percentage. Unless otherwise specified, continuous outcome variables were reported as mean±SD, and categorical outcome variables were reported as number and percentage. Significance testing with respect to changes from baseline along continuous measures was accomplished by means of the Wilcoxon signed rank test, or, the paired samples t-test. Also, when assessing within-group changes from baseline following intervention, where the variable of interest was dichotomous, the McNemar test was employed. When significant differences were noted, 95% confidence intervals (Cis) were calculated for mean differences in pre/post physician-rated UI severity scale scores. Chi square and Fisher's exact tests were used to investigate between-group differences on categorical variables. Between-group comparisons on continuous measures were carried out by means of parametric and nonparametric tests, as appropriate (i.e., independent samples t-test; Mann-Whitney U-test or Kruskal-Wallis test). Treatment effects were further assessed by performing subgroup analyses using the variables of % UI improvement and % retention of treatment effect as dependent measures. Associations between demographic, treatment, and outcome variables were examined using standard Pearson correlation methods. In addition, bivariate unadjusted analyses were performed to identify patient characteristics and treatment variables associated with achieving treatment success threshold; logistic regression was applied in the development of a predictive, multivariate model.

Results

Baseline Patient Characteristics

Table 2 presents baseline characteristics of the total UI patient group (n=108). Table 3 shows baseline characteristics of patients undergoing the treatment (TG, n=98, SUI+ Mixed) and patients undergoing the sham intervention (CG, n=10). The two groups did not differ significantly on 10 of 11 relevant baseline variables. A significant difference was found between groups when assessing percentages that reported performing Kegels (TG 7.1% vs CG 60%; p<0.001). When the TG was divided into SUI and Mixed, no significant differences were found between the CG vs SUI or CG vs Mixed.

TABLE 2

Baseline characteristics of female patients with urinary incontinence

| Characteristic | Patient Group (n = 108) |
|---|---|
| Age, mean ± SD, yrs (range) | 55.4 ± 14.4 (28-87) |
| UI severity rating scale, mean ± SD (range) | 3.6 ± 1.4 (1-6) |
| Vaginal birth, mean ± SD (range) | 2.2 ± 1.7 (0-11) |
| Weight status*, N (%) | |
| Normal | 78 (72.2) |
| Overweight | 19 (17.6) |
| Obese | 11 (10.2) |
| Menopause status, N (%) | |
| Pre-menopausal | 26 (24.1) |
| Peri-menopausal | 16 (14.8) |
| Post-menopausal | 66 (61.1) |
| Urogenital surgery | 18 (17.0) |
| Gynecologic surgery | 36 (33.0) |
| Exam findings, N (%) | |
| Urethral hypermobility (UH) | 3 (2.8) |
| Urethra open (UO) | 22 (20.4) |
| UH + UO | 83 (76.8) |
| UI status, N (%) | |
| SUI | 58 (53.7) |
| Mixed | 50 (46.3) |
| Performing Kegel exercise, N (%) | 13 (12.0) |
| Pre-treatment activity level without leak† | |
| High pressure | 0 (0.0) |
| Low pressure | 54 (50.0) |
| Walking | 27 (25.0) |
| None | 27 (25.0) |
| Pad usage‡, N (%) | 79 (73.2) |

SD, standard deviation; UI, urinary incontinence; SUI, stress urinary incontinence; Mixed, stress and urge incontinence groups mixed.
*Weight ranges stipulated by the NIH consensus development conference statement. Gastrointestinal surgery for severe obesity. Obes Surg 1991; 1: 243-256.
†High pressure (jump, run, cough, sneeze, lift, exercise high impact); Low Pressure (laugh, reach, get up out of a chair, bend, exercise low impact); Walking (able to walk); None (no activities can be performed without leaking urine)
‡Pad use ranged from 1 thin pad/day up to 5 maximum size pads/day

TABLE 3

Baseline characteristics of treatment group vs control group

| Variable | Treatment Group (n = 98) | Control Group (n = 10) | P-value |
|---|---|---|---|
| Age, mean ± SD, yrs (range) | 55.0 ± 14.2 (28-87) | 58.9 ± 15.8 (39-85) | NS* (0.47) |
| UI severity rating scale, mean ± SD (range) | 3.6 ± 1.4 (1-6) | 3.8 ± 1.6 (2-6) | NS* (0.80) |
| Vaginal birth, mean ± SD (range) | 2.3 ± 1.7 (0-11) | 1.3 ± 1.5 (0-4) | NS* (0.08) |

TABLE 3-continued

Baseline characteristics of treatment group vs control group

| Variable | Treatment Group (n = 98) | Control Group (n = 10) | P-value |
|---|---|---|---|
| Weight status, N (%) | | | NS† (0.98) |
| Normal | 71 (72.4) | 7 (70.0) | |
| Overweight | 17 (17.3) | 2 (20.0) | |
| Obese | 10 (10.2) | 1 (10.0) | |
| Menopause status, N (%) | | | NS† (0.82) |
| Pre-menopausal | 24 (24.5) | 2 (20.0) | |
| Peri-menopausal | 15 (15.3) | 1 (10.0) | |
| Post-menopausal | 59 (60.2) | 7 (70.0) | |
| Urethral hypermobility, N (%) | 78 (79.6) | 8 (80.0) | NS‡ (0.99) |
| Urethral open status, N (%) | 95 (96.9) | 10 (100.0) | NS‡ (0.99) |
| UI status, N (%) | | | NS‡ (0.99) |
| SUI | 53 (54.1) | 5 (50.0) | |
| Mixed | 45 (45.9) | 5 (50.0) | |
| Performing Kegel exercise, N (%) | 7 (7.1) | 6 (60.0) | <0.001‡ |
| Leak on walking and/or inactivity, N (%) | 49 (50.0) | 6 (60.0) | NS‡ (0.74) |
| Pad usage, N (%) | 73 (74.5) | 6 (60.0) | NS‡ (0.45) |

SD, standard deviation; UI, urinary incontinence; SUI, stress urinary incontinence; Mixed, stress and urge incontinence groups mixed.
*Independent samples Mann-Whitney U test
†Chi square test
‡Fisher's exact test Safety There were no major, and relatively few minor, complications during or following treatments. Seven of 98 (7.1%) experienced temporary decreased holding capacity, and 1/98 (1.0%) experienced a urinary tract infection, readily treated with antibiotics. Infrared light penetration of the skin (1-3 mm) caused no burning, pain, or swelling of the skin, and thus, no recovery time was needed.

Outcomes

Mean procedure time for the TG was 53 minutes (range 45-60), 18 minutes (15-20) for the CG, Following sham treatment, CG showed no significant change in UI severity relative to baseline (3.8±1.6 vs 3.8±1.6; NS). In contrast, the TG showed a statistically significant difference between baseline and post-treatment UI severity scores (3.6±1.4 vs 1.3±1.3; p<0.001; 95% CI, 2.1-2.6). Patients receiving 3-4 ILTs (n=35 [36%]) moved from a mean baseline UI severity rating of 3.5±1.3 to 0.6±0.8 (p<0.0001; 95% CI, 2.5-3.2). There was a significant proportional change in UH status in the TG (baseline, 79.6% [78/98] diagnosed with UH vs post-treatment, 39.8% [39/98]; p<0.001), but no change in the CG.

Adjunctive to physical examination findings showing improved UI, photographic evidence demonstrated that 100% of TG patients experienced skin laxity reduction (examples in FIGS. 14 and 15). All TG patients reported UI improvement (mean 78.2±22.9%; range 20%-100%) principally in the form of urinary control (100%) and holding capacity (81%); the CG reported 0% UI improvement, No CG patient reported any form of UI improvement; however, five showed transient improvement in skin laxity.

Table 4 presents results of between-group statistical comparisons on outcome variables at 1-3 months post last treatment, TG UI severity rating was significantly lower than that of the CG (1.3±1.3 vs 3.8±1.6; p<0.001), and the percentage of TG patients with UH post treatment was significantly lower than that of CG patients (39% vs 80%; p<0.05). The TG achieved a significantly lower percentage of urethra open ("UO") status patients than the CG (54.1% vs 100%; p<0.01) and a much lower percentage of patients reporting UI at very low levels of activity (12.2% vs 70%; p<0.01). Although any form of TG pad use dropped from 74.5% to 42.9%, representing a significant within-group change (p<0.01), the difference in proportions between groups did not reach statistical significance (NS, p=0.33). Although baseline differences existed between groups in the proportion of patients performing Kegels (TG [7.1%] vs CG [60%]), following intervention, the significant difference was no longer apparent (50% vs 60%; NS). The percentage of TG patients performing Kegels significantly increased from 7.1% to 50% (p<0.001).

The lower portion of Table 4 depicts the TG subdivided into SUI (n=53) and Mixed (n=45). UI improvement was 81.8% for SUI, 73.9% Mixed. Analysis of mean differences in UI improvement between SUI, Mixed, and the CG indicated that significant differences existed (p<0.001). While both SUI and Mixed groups differed significantly from CG, post hoc tests showed that no differences existed between SUI and Mixed. In UI severity, the SUI group had a post-treatment rating of 0.9, while Mixed and CG had ratings of 1.7 and 3.8, respectively. Both SUI and Mixed had significantly lower UI severity ratings post treatment relative to CG (p<0.001); SUI also differed significantly from Mixed in post-UI severity (p<0.01).

TABLE 4

Outcomes at 1-3 months post last infrared light treatment

| Variable | Treatment Group (n = 98) | Control Group (n = 10) | P-value |
|---|---|---|---|
| UI severity scale, mean ± SD (range) | 1.3 ± 1.3 (0.0-5.0) | 3.8 ± 1.6 (2.0-6.0) | <0.001* |
| UI % improvement, mean ± SD (range) | 78.2 ± 22.9 (20.0-100.0) | 0.0 ± 0.0 (0.0-0.0) | <0.001* |
| UH, N (%) | 39 (39.8) | 8 (80.0) | <0.05† |
| Perform Kegels, N (%) | 49 (50.0) | 6 (60.0) | NS† (0.74) |
| UO, N (%) | 53 (54.1) | 10 (100.0) | <0.01† |
| UI at low activity, N (%) | 12 (12.2) | 7 (70.0) | <0.01† |
| Pad usage, N (%) | 42 (42.9) | 6 (60.0) | NS† (0.33) |

| | SUI Group (n = 53) | Mixed Group (n = 45) | Control Group (n = 10) | P-value |
|---|---|---|---|---|
| UI severity scale, mean ± SD | 0.9 ± 1.0 | 1.7 ± 1.6 | 3.8 ± 1.6 | <0.001‡ |
| UI % improvement, mean ± SD | 81.8 ± 20.6 | 73.9 ± 24.9 | 0.0 ± 0.0 | <0.001‡ |
| Imp. or resolved UH, N (%)§ | 30 (78.9) | 22 (55.0) | 0 (0.0) | <0.01† |
| Imp. Kegel performance, N (%) | 45 (84.9) | 34 (75.6) | 0 (0.0) | <0.001† |
| Imp. UI, N (%) | 53 (100.0) | 45 (100.0) | 0 (0.0) | <0.001† |
| Imp. hold capacity, N (%) | 40 (75.5) | 39 (86.7) | 0 (0.0) | <0.001† |
| Imp. Control, N (%) | 53 (100.0) | 45 (100.0) | 0 (0.0) | <0.001† |
| Imp. tx area support, N (%) | 22 (41.5) | 12 (26.7) | 0 (0.0) | NS† (0.10) |
| Imp. skin laxity, N (%) | 53 (100.0) | 45 (100.0) | 5 (50.0) | <0.001† |
| Imp. sensation, N (%) | 18 (34.0) | 11 (24.4) | 0 (0.0) | NS† (0.18) |
| Imp. or resolved UO, N (%)§ | 21 (42.0) | 24 (53.3) | 0 (0.0) | <0.05† |

Highlighted variables represent success threshold criteria.
SD, standard deviation; UI, urinary incontinence; SUI, stress urinary incontinence; Mixed, stress and urge incontinence groups mixed; Imp., improved; Tx, treatment; UH, urethral hypermobility; UO, urethra open.
*Independent samples Mann-Whitney U test
†Fisher's exact test
‡Independent samples Kruskal-Wallis test
§Percentage calculations based on total patients presenting with UH and/or OH.
Note:
significant p-values in the lower half of the table indicate that both SUI and Mixed groups statistically differed from the control group in independent testing; p-values represent least significant difference.

SUI and Mixed groups experienced significant change from baseline UI severity. The SUI group changed from a mean 3.2±1.3 to a post-treatment UI severity rating of 0.9±1.0 (p<0.001; 95% CI, 2.0-2.6); while Mixed went from 4.2±1.7 to 1.7±1.6 (p<0.001; 95% CI, 2.1-2.8).

As shown in Table 4, the CG showed virtually no improvement in the wide array of variables assessed. Between-group differences were found in nearly all variables (exceptions: treatment area support [NS, p=0.10]; sensation [NS, p=0.18]), with both SUI and Mixed groups demonstrating significantly higher rates of improvement compared to CG.

At first follow-up, 64% of TG had received 1-2 ILTs. An average of 90.0% SUI/81.6% Mixed UI improvement was reported by patients receiving 4 treatments; 91.4%/92.8% improvement, 3 treatments; 88.1%/64.7%, 2 treatments; and 69.8%/53.8%, after 1 treatment. Of SUI/Mixed patients, 78.9%/55% were resolved or improved in UH: UH completely resolved in 100%/50% undergoing 4 treatments; 80%/86.7% of those undergoing 3 treatments, 20%/43.8% undergoing 2, and 75%/14.3% undergoing one treatment. Only 8 (21%) SUI patients experienced no change in UH, and, at follow-up, each had only undergone one treatment. Sanitary pad usage dropped from 74.5% to 42.9% (p<0.001) in the overall TG (Tables 2, 4) with no significant change in the CG, In the SUI patient group, 32.1% reported having never used pads to help manage UI/leaking; instead, these patients chose to change clothing when necessary. At baseline, 67.9% SUI/84.4% Mixed patients reported using pads to manage UI. Following treatment, including all patients reporting pad usage and undergoing 1-4 treatments: 52.7% SUI/36.8% Mixed stopped all pad use; 25.0% SUI/18.4% Mixed reported using smaller and fewer pads; 16.0% SUI/39.8% Mixed used fewer pads; and 5.5% SUI/5.3% Mixed reported no change in pad use.

Additional qualitative treatment impact was noted when assessing change from baseline in activity levels that patients could engage in without experiencing leaking (Table 2). Of SUI/Mixed patients, respectively, undergoing 1-4 treatments, 81.0%/66.0% advanced 1 activity level; 11.2%/22.2% 2 levels, 5.6%/11.1% 3 levels; and 1 SUI patient (1.8%) showed no activity improvement. Of SUI/Mixed patients that improved 1 activity level, 66.0%/28.9% advanced from the low-pressure to high-pressure activity level; 13.2%/13.3% from walking to low-pressure activity; and 1.8%/24.4% from no activity to walking without leakage. Of SUI/Mixed patients that improved 2 or more activity levels, 5.6%/17.8% advanced from walking to high-pressure activity level; 5.6%/4.4% from no activity to low-pressure activity; and 5.6%/11.1% from no activity to high-pressure activity. Of interest, treatment also demonstrated consistent, non-surgical reduction or resolution of vaginal prolapse, external hemorrhoids, cystocele, rectocele, and rectal incontinence.

Subgroup Analyses

Table 5 presents findings from subgroup analyses of % UI improvement at 1-3 (median=1.0) months post last treatment (follow-up time point 1) in conjunction with % UI retention of effect at 1-16 (median=10.0) months post last treatment (follow-up time point 2). Overall TG & UI improvement was 78.2% and overall retention of treatment effect, 92.7%. Regarding subgroup differences in % UI improvement, analysis of variance tests indicated significant differences between age groups (p<0.05), menopause groups (p<0.01), and number-of-treatments groups (p<0.001). Post hoc tests revealed a statistical difference between the <43 age group and the ≥65 age group, with the younger patients reporting significantly higher levels of % UI improvement following treatment (89.2±14.7 vs 68.6±23.4; p<0.01). Similarly, the only significant difference between menopause groups was found between the pre- and post-menopause groups, with the pre-menopause group reporting higher levels of % UI improvement (90.0±13.2 vs 73.8±23.9; p<0.01). In addition, patients having received only 1 ILT reported significantly lower % UI improvement than patients undergoing three treatments (65.3±24.7 vs 92.2±12.2; p<0.0001). A second statistically significant difference was found between patients undergoing 2 vs 3 ILTs: those patients experiencing three treatments reported significantly higher levels of % UI improvement (92.2±12.2 vs 75.7±23.2; p<0.05). The only other statistically significant subgroup difference with respect to % UI improvement was found between patients experiencing complete UH resolution and those that did not. Complete UH resolution contributed to significantly higher % UI improvement ratings (92.8±9.5 vs 57.3±20.7; p<0.001). Regarding retention of % UI improvement at second follow-up, significant subgroup differences were found between UH resolution groups, Kegel performance groups, and menopause groups (omnibus test, p<0.05). Patients experiencing UH resolution vs those that did not (95.1±11.2 vs 86.3±24.6; p=0.05), and patients that habitually performed Kegels vs those that did not (98.9±5.3 vs 86.5±23.7; p<0.001), reported significantly higher levels of retention of treatment effect. In addition, pre-menopause patients reported significantly higher levels of retention than post-menopause patients (99.6±2.0 vs 89.8±21.6; p<0.01).

TABLE 5

Sub-group analysis of urinary incontinence improvement at 1-3 months post first infrared light treatment and retention at 1-16 months

| Variable | N | UI Improvement (Mean ± SD) | P-value | UI Retention of Improvement (Mean ± SD) | P-value |
|---|---|---|---|---|---|
| Overall | 98 | 78.2 ± 22.9 | — | 92.7 ± 18.2 | — |
| UI group | | | | | |
| SUI | 53 | 81.8 ± 20.6 | NS* (0.09) | 93.4 ± 17.6 | NS* (0.69) |
| Mixed | 45 | 73.9 ± 24.9 | | 91.9 ± 19.1 | |
| Prior surgery | | | | | |
| Yes | 51 | 78.3 ± 21.9 | NS* (0.94) | 92.6 ± 20.6 | NS* (0.93) |
| No | 47 | 78.0 ± 24.2 | | 92.9 ± 15.4 | |
| Weight status* | | | | | |
| Normal | 71 | 80.6 ± 21.3 | NS† (0.17) | 93.5 ± 16.9 | NS† (0.29) |
| Overweight | 17 | 74.1 ± 25.8 | | 96.5 ± 7.0 | |
| Obese | 10 | 68.0 ± 27.4 | | 81.0 ± 32.8 | |
| Age group | | | | | |
| <43 yrs | 24 | 89.2 ± 14.7 | <0.05† | 99.6 ± 2.0 | NS† (0.10) |
| 43-<55 | 24 | 79.8 ± 23.8 | | 88.5 ± 24.6 | |
| 55-<65 | 25 | 75.6 ± 24.4 | | 91.0 ± 16.1 | |
| ≥65 | 25 | 68.6 ± 23.4 | | 91.8 ± 20.8 | |
| Menopause group | | | | | |
| Pre | 24 | 90.0 ± 13.2 | <0.05† | 99.6 ± 2.0 | <0.05† |
| Peri | 15 | 76.3 ± 25.6 | | 93.0 ± 15.6 | |
| Post | 59 | 73.8 ± 23.9 | | 89.8 ± 21.6 | |
| UH resolution | | | | | |
| Complete | 39 | 92.8 ± 9.5 | <0.001* | 95.1 ± 11.2 | 0.05* |
| No change | 26 | 57.3 ± 20.7 | | 86.3 ± 24.6 | |
| Kegel performance | | | | | |
| Yes | 49 | 80.5 ± 21.1 | NS‡ (0.54) | 98.9 ± 5.3 | <0.001‡ |
| No | 49 | 75.8 ± 24.6 | | 86.5 ± 23.7 | |
| No. tx groups | | | | | |
| 1 tx | 29 | 65.3 ± 24.7 | <0.001* | 89.7 ± 22.8 | NS* (0.35) |
| 2 tx | 34 | 75.7 ± 23.2 | | 90.7 ± 20.7 | |
| 3 tx | 30 | 92.2 ± 12.2 | | 97.3 ± 8.3 | |
| 4 tx | 5 | 85.0 ± 13.2 | | 96.0 ± 8.9 | |

TABLE 5-continued

Sub-group analysis of urinary incontinence improvement at 1-3 months post first infrared light treatment and retention at 1-16 months

| Variable | N | UI Improvement (Mean ± SD) | P-value | UI Retention of Improvement (Mean ± SD) | P-value |
|---|---|---|---|---|---|
| Days between tx | | | | | |
| <30 | 78 | 77.1 ± 23.5 | NS‡ (0.47) | 92.2 ± 19.4 | NS‡ (0.75) |
| ≥30 | 20 | 82.3 ± 20.3 | | 94.8 ± 12.7 | |

SD, standard deviation; UI, urinary incontinence; SUI, stress urinary incontinence; UI Mixed, stress and urge incontinence groups mixed; tx, treatment.
*Independent samples t-test
†Independent samples Kruskal-Wallis test
‡Independent samples Mann-Whitney U test Correlation Analyses Patient age and number of vaginal births were negatively related to perceived % UI improvement (r=−0.33; p<0.01; r=−0.25, p<0.05). Patient age and number of vaginal births were also positively related to baseline UI severity rating (r=0.50; p<0.001; r=0.33; p<0.001). Baseline UI severity rating was negatively related to % UI improvement (r=−0.50; p<0.001) and positively related to post-treatment severity rating (r=0.66; p<0.001). Post-treatment UI severity rating was negatively related to number of treatments received (r=−0.31; p<0.01). Number of treatments was also positively related to average number of days between treatments and to % UI improvement (r=0.39; p<0.001; r=0.43; p<0.001). Interestingly, number of treatments was not significantly related to retention of benefit (r=0.17, p=0.11). Average days between treatments was negatively related to post-treatment UI severity rating (r=−0.21; p<0.05) and positively related to % UI improvement (r=0.23; p<0.05).

Treatment benefit retention was not significantly related to patient age (r=−0.15, p=0.15) or number of vaginal births (r=−0.20, p=0.051), treatments (r=0.17, p=0.11), or average days between treatments (r=0.12, p=0.23). However, retention of benefit was negatively related to pre- and post-treatment UI severity ratings (r=−0.26, p=0.05; r=−0.38, p=0.11), and positively related to % UI improvement (r=0.35, p=0.001).

Bivariate Analyses and Logistic Regression

Success threshold criteria were used to establish two outcome groups: those who achieved success (n=53, 54.1%) vs those that did not (n=45, 45.9%). Between-group differences were analyzed to identify potential predictors of outcome success: age (52.0±13.6 vs 58.6±14.2, success vs no-success groups, respectively; p<0.05); vaginal births (1.9±1.2 vs 2.6±2.1; p<0.05); number of treatments (2.5±0.8 vs 1.6±0.8; p<0.0001); baseline UI rating (3.1±1.3 vs 4.2±1.2; p<0.0001); average number of days between treatments (24.7±26.8 vs 11.5±15.7; p<0.01). Logistic regression analysis demonstrated that when the above variables and certain variables of interest (i.e., weight and menopause status, previous surgery, UI type, and average number of pulses per ILT) were factored into the multivariate model, only patient baseline UI severity and number of treatments were independently predictive of achieving success threshold (baseline UI severity variable: Wald's statistic=9.08, p<0.01, b coefficient=−0.99, OR=0.37, 95% CI, 0.20-0.71; number of treatments variable: Wald's statistic=17.17; p<0.0001, b coefficient=−2.23, OR=9.30, 95% CI, 3.24-26.61.

Study Findings

In the study, there were no reports of burn, skin injury, over-tightening, fat necrosis, or scarring. ILT demonstrated safety with no recovery time or complication. All patients receiving the procedure reported improvement in UI, ranging from 20%-100% (mean 78.2%), largely dependent on number of treatments received. Physician examination of UH and calibrated photographic data of the external genitals provided objective evidence that corroborated TG reporting of UI improvement in contrast to the CG with no improvement in UI, no change in UH, and no increased ability to perform Kegels.

Patient QoL improved dramatically, primarily in the form of increased freedom to re-engage in desired life activities without fear of leaking. At follow-up, only 12.2% of the TG experienced UI at low levels of activity compared to 70% in the CG. Of the TG, 99% advanced at least 1 activity level, with some patients advancing from the lowest activity level (no activity without leak) to the highest level (able to perform high-pressure activities). The TG also achieved significant reduction in sanitary pad use and/or the need to change clothing, Nearly half of the TG (45%) stopped pad use altogether; only 5% reported no change in pad usage. An additional advantage of the procedure was its consistent reduction or resolution of vaginal prolapse, external hemorrhoids, and rectal incontinence.

Regardless of UI type, weight status, or prior urogenital/gynecologic surgery, patients were shown to achieve equally favorable outcomes. Although younger, premenopausal patients tended to report higher levels of overall UI improvement and benefit retention, all age groups experienced significant UI improvement. The oldest group (65-89 years) reported lower UI improvement than the youngest (24-<43), yet, these patients can expect UI improvement comparable to that of middle-aged patients (43-<65). Older patients were also shown to have higher baseline UI severity, thereby moderating their rate of UI improvement.

Results of logistic regression analysis indicated that, at baseline, for each point increase in the 6-point UI severity scale, the odds that the success threshold will not be achieved are nearly tripled (2.70). Conversely, with each ILT (1-4), the odds of achieving success threshold are increased by a factor of 9.30. This suggests that (older) patients presenting with the highest UI severity ratings likely require 3-4 ILTs to reach treatment endpoint. In fact, at first follow-up, 61% of patients presenting with extreme baseline UI severity ratings (5-6) had undergone only 1-2 ILTs; of these patients; 32% had already achieved success threshold.

Moreover, the treatment group received 1-4 ILTs, thereby attenuating overall efficacy results; but also, observing results for a range of 1-4 treatments facilitated assessment of treatment effectiveness, vis-à-vis number of treatments. This study conclusively demonstrated that the more ILTs, the lower the post-treatment UI severity and the greater the UI improvement. Each additional ILT augmented patients' likelihood of achieving treatment endpoint nearly ten-fold. A subset of patients who did not achieve success threshold after 1-2 treatments, and who waited >3 months for additional treatments, began to lose their initial toning effect and % UI improvement.

Over 600 procedures have been performed to date with reliable outcomes in the treatment of SUI and Mixed UI. The treatment's minimum success rate for patients achieving treatment goal is 70% leak improvement; maximum success rate is 100%; the vast majority of patients achieved >85% overall continence improvement. SUI continues to be treated with slightly better outcomes than Mixed, yet all patients average >85% overall success. Retention of results continues to be excellent, and patients are now instructed in a home program of pelvic muscle training that appears to have enabled 100% of patients to retain the full benefit of their treatment.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as concentration, clinical conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described,

The invention claimed is:

1. A method of reducing and toning skin of a clitoral hood of a human patient, the method comprising performing a plurality of passes each comprising:
applying mineral powder to skin within first, second, and third treatment areas, the skin in the first treatment area being above the clitoral hood, the skin in the second treatment area being along a first side of the clitoral hood, and the skin in the third treatment area being along a second side of the clitoral hood, the second and third treatment areas each being laterally alongside the clitoral hood;
applying a gel atop the mineral powder to cool the skin in the first, second, and third treatment areas;
heating the skin in the first, second, and third treatment areas using infrared light; and
removing the mineral powder and the gel from the skin in the first, second, and third treatment areas.

2. The method of claim 1, wherein heating the skin in the first, second, and third treatment areas comprises:
placing an infrared light generating device against the skin in the first treatment area, applying moderate pressure, and actuating the infrared light generating device to thereby cause the infrared light generating device to deliver the infrared light to the skin in the first treatment area;
placing the infrared light generating device against the skin in the second treatment area, applying moderate pressure, and actuating the infrared light generating device to thereby cause the infrared light generating device to deliver the infrared light to the skin in the second treatment area; and
placing the infrared light generating device against the skin in the third treatment area, applying moderate pressure, and actuating the infrared light generating device to thereby cause the infrared light generating device to deliver the infrared light to the skin in the third treatment area.

3. The method of claim 2, wherein the infrared light generating device is orientated horizontally when placed against the skin in the first treatment area, and the infrared light generating device is orientated vertically when placed against the skin in the second and third treatment areas.

4. The method of claim 2, wherein the infrared light generating device includes a sapphire crystal, the sapphire crystal is against the skin in the first treatment area when the infrared light generating device is placed the against the skin in the first treatment area the sapphire crystal is against the skin in the second treatment area when the infrared light generating device is placed the against the skin in the second treatment area, and the sapphire crystal is against the skin in the third treatment area when the infrared light generating device is placed the against the skin in the third treatment area.

5. The method of claim 2, wherein the infrared light generating device delivers the infrared light to the skin in each of the first, second, and third treatment areas as a pulse that has a duration of approximately six to eight seconds.

6. The method of claim 2, further comprising:
setting the infrared light generating device to 30-55 Joules/cm$^2$.

7. The method of claim 1, wherein the infrared light heats the skin to a depth of 1 millimeter to 3 millimeters.

8. The method of claim 1, wherein applying the gel comprises applying approximately a quarter inch of the gel.

9. The method of claim 1, wherein the gel is ultrasound gel that has been refrigerated.

10. The method of claim 1, wherein the gel cools the skin to a temperature of less than 40 degrees.

11. The method of claim 1, wherein the mineral powder comprises micronized zinc oxide, micronized titanium dioxide, mica, and 1% salicylic acid powder.

12. A method of reducing and toning skin of a clitoral hood of a human patient, the method comprising:
applying a mineral powder to skin within first, second, and third treatment areas, the skin in the first treatment area being above the clitoral hood, the skin in the second treatment area being along a first side of the clitoral hood, and the skin in the third treatment area being along a second side of the clitoral hood, the second and third treatment areas each being laterally alongside the clitoral hood;
applying a gel atop the mineral powder in the first, second, and third treatment areas;
heating the skin in the first treatment area with an infrared light generating device;
repositioning the infrared light generating device and heating the skin in the second treatment area with the infrared light generating device;
repositioning the infrared light generating device and heating the skin in the third treatment area with the infrared light generating device; and
removing the mineral powder and the gel from the skin in the first, second, and third treatment areas.

13. The method of claim 12, wherein heating the skin in the first treatment area comprises placing the infrared light generating device against the skin in the first treatment area, applying moderate pressure, and actuating the infrared light generating device to thereby cause the infrared light generating device to deliver the infrared light to the skin in the first treatment area;
heating the skin in the second treatment area comprises placing the infrared light generating device against the skin in the second treatment area, applying moderate pressure, and actuating the infrared light generating device to thereby cause the infrared light generating device to deliver the infrared light to the skin in the second treatment area; and
heating the skin in the third treatment area comprises placing the infrared light generating device against the skin in the third treatment area, applying moderate pressure, and actuating the infrared light generating device to thereby cause the infrared light generating device to deliver the infrared light to the skin in the third treatment area.

14. The method of claim 13, wherein the infrared light generating device is orientated horizontally when placed against the skin in the first treatment area, and the infrared light generating device is orientated vertically when placed against the skin in the second and third treatment areas.

15. The method of claim 13, wherein the infrared light generating device includes a sapphire crystal, the sapphire crystal is against the skin in the first treatment area when the infrared light generating device is placed the against the skin in the first treatment area, the sapphire crystal is against the skin in the second treatment area when the infrared light generating device is placed the against the skin in the second treatment area, and the sapphire crystal is against the skin in the third treatment area when the infrared light generating device is placed the against the skin in the third treatment area.

16. The method of claim 12, wherein the infrared light generating device delivers the infrared light to the skin in each of the first, second, and third treatment areas as a pulse that has a duration of approximately six to eight seconds.

17. The method of claim 12, further comprising:
setting the infrared light generating device to 30-55 Joules/cm².

18. The method of claim 12, wherein the infrared light heats the skin to a depth of 1 millimeter to 3 millimeters.

19. The method of claim 12, wherein applying the gel comprises applying approximately a quarter inch of the gel atop the mineral powder in the first, second, and third treatment areas.

20. The method of claim 12, wherein the gel is ultrasound gel that has been refrigerated.

21. The method of claim 20, wherein the gel cools the skin to a temperature of less than 40 degrees.

22. The method of claim 12, wherein the mineral powder comprises micronized zinc oxide, micronized titanium dioxide, mica, and 1% salicylic acid powder.

\* \* \* \* \*